US006887698B2

(12) United States Patent
Jalkanen et al.

(10) Patent No.: US 6,887,698 B2
(45) Date of Patent: May 3, 2005

(54) GLUCURONYL C5-EPIMERASE, DNA ENCODING THE SAME AND USES THEREOF

(75) Inventors: Markku Jalkanen, Piispanristi (FI); Kamel El Darwish, Turku (FI); Ulf Lindahl, Uppsala (SE); Jin-ping Li, Uppsala (SE)

(73) Assignees: Biotie Therapies Corp., Turku (FI); Inalco S.p.A., Milan (IT)

( * ) Notice: Subject to any disclaimer, the term of this patent is extended or adjusted under 35 U.S.C. 154(b) by 302 days.

(21) Appl. No.: 10/005,647

(22) Filed: Dec. 7, 2001

(65) Prior Publication Data

US 2002/0127696 A1 Sep. 12, 2002

Related U.S. Application Data

(60) Provisional application No. 60/304,180, filed on Dec. 8, 2000.

(51) Int. Cl.$^7$ .............................. C12N 15/61; C12N 9/90

(52) U.S. Cl. ................. 435/233; 435/320.1; 435/252.7; 536/27.2

(58) Field of Search .......................... 435/320.1, 252.7, 435/233; 536/23.2

(56) References Cited

U.S. PATENT DOCUMENTS

| 5,939,289 A | 8/1999 | Ertesv.ang.g et al. |
| 6,372,477 B1 | 4/2002 | J.theta.rsboe et al. |

FOREIGN PATENT DOCUMENTS

| JP | WO 01/38507 | 5/2001 |
| WO | WO 96/14425 | 5/1996 |
| WO | WO 98/48006 | 10/1998 |

OTHER PUBLICATIONS

Li, J–P, et al. (2003) J. Blol. Chem. 278(31), 28363–28366.*
Campbell, P. et al., "Biosynthesis of Heparin/Heparan Sulfate: Purification of the p–Glucuronyl C–5 Epimerase from Bovine Liver," *J. Biol. Chem.* 269:26953–26958, The American Society of Biochemistry and Molecular Biology Inc. (1994).
Casu, B. et al., "Conformational flexibility: a new concept for explaining binding and biological properties of iduronic acid–containing glycosaminoglycans," *Trends Biochem. Sci.* 13:221–225, Elsevier Science Ltd. (1988).
Kelley, L.A. et al., "Enchanced Genome Annotation Using Structural Profiles in the Program 3D–PSSM," *J. Mol. Biol.* 299:499–520, Academic Press (Jun. 2000).
Kjellén, L. and Lindahl, U., "Proteoglycans: Structures and Interactions," *Annu. Rev. Biochem.* 60:443–475, Annual Reviews Inc. (1991).

Li, J.–p. et al., "Biosynthesis of Heparin/Heparan Sulfate. cDNA Cloning and Expression of D–Glucuronyl C5–Epimerase from Bovine Lung.," *J. Biol. Chem.* 272:28158–28163, The American Society for Biochemistry and Molecular Biology, Inc. (1997).
Malmström, A. et al., "Biosynthesis of Heparin. Partial Purification of the Uronosyl C–5 Epimerase," *J. Biol. Chem.* 255:3878–3883, American Society of Biochemistry and Molecular Biology Inc. (1980).
Ron, D. et al., "Expression of Biologically Active Recombinant Keratinocyte Growth Factor. Structure/Function Analysis of Amino–Terminal Truncation Mutants," *J. Biol. Chem.* 268:2984–2988, American Society of Biochemistry Molecular Biology Inc. (1993).
Salmivirta, M. et al., "Heparan sulfate: a piece of information," *FASEB J.* 10:1270–1279, Federation of American Societies for Experimental Biology (1996).
Wilson, R. et al., "2.2 Mb of contiguous nucleotide sequence from chromosome III of *C. elegans*," *Nature* 368:32–38, Macmillan Magazine Limited (1994).
Voet, D. and Voet, J.G., "Biochemistry," $2^{nd}$ Edition, John Wiley and Sons, Inc., New York, NY, p. 965–967 (1995).
Xu, F. and Cooley, L., "kelch Encodes a Component of Intercellular Bridges in Drosophila Egg Chambers," *Cell* 72:681–693, Cell Press (1993).
NCBI Entrez, GenBank Report, Accession No. LO8483, from Xue, F. et al. (1993).
NCBI Entrez, GenBank Report, Accession No. P46555, from Sulston, J. (1994).
NCBI Entrez, GenBank Report, Accession No. AF043700, from Wilson, R. et al. (1998).
NCBI Entrez, GenBank Report, Accession No. AAF36018, from The *C. elegans* Sequencing Consortium et al. (1998).
NCBI Entrez, GenBank Report, Accession No. AAF57373, from Adams, M.D. et al. (Mar. 2000).
Féthière, J. et al., "Crystal Structure of Chondroitin AC Lyase, a Representative of a family of Glycosaminoglycan Degrading Enzymes," *J. Mol. Biol.* 288:635–647, Academic Press (May 1999).
Crawford, B.E. et al., "Cloning, Golgi Localization, and Enzyme Activity of the Full–length Heparin/Heparan Sulfate–Glucuronic Acid C5–epimerase", *J. Biol. Chem.* 276:21538–21543, The American Society for Biochemistry and Molecular Biology Inc. (Jun. 2001).

(Continued)

*Primary Examiner*—Charles L. Patterson, Jr.
(74) *Attorney, Agent, or Firm*—Sterne, Kessler, Goldstein & Fox, P.L.L.C.

(57) ABSTRACT

The invention is directed to a novel purified mouse C5-epimerase, fragments thereof, nucleic acids encoding the same and the recombinant production thereof. The invention is also directed to fragments of such epimerase, especially N-terminal fragments that are useful in fusion protein constructs to enhance the activity of recombinantly-produced heterologous epimerase enzymes.

15 Claims, 13 Drawing Sheets

OTHER PUBLICATIONS

Li, J.P. et al., "Characterization of the D–Glucuronyl C5–epimerase Involved in the Biosynthesis of Heparin and Heparan Sulfate", *J. Biol. Chem.* 276:20069–20077, The American Society for Biochemistry and Molecular Biology, Inc. (Jun. 2001).

PCT Partial International Search Report for PCT/FI01/01068, filed Dec. 7, 2001, Biotie Therapies Corp. (Search Report mailed Aug. 1, 2002).

Hagner–McWhirter, Å. et al., "Biosynthesis of heparin/heparin sulfate kinetic studies of the glucuronyl C5–epimerase with N–sulfated derivatives of the *Esherichia coli* K5 capsular polysaccharide as substrates," Glycobiology 10:159–171, Oxford University Press (Feb. 2000).

Hagner–McWhirter, Å. et al., "Biosyntheis of heparin/heparan sulphate: mechanism of epimerization of glucuronyl C–5," *Biochem J.* 347:69–75, London Portland Press On Behalf Of The Biochemical Society (Apr. 2000).

Nagase, T. et al., "Prediction of the Coding Sequences of Unidentified Human Genes. XII. The Complete Sequences of 100 New cDNA Clones from Brain Which Code for Large Proteins in vitro," *DNA Res.* 5:355–364, Tokyo Kazusa DNA Research Institute and Universal Academy Press (1998).

D–glucuronyl C5–epimerase (EC 5.1.3.–) amino acid sequence (mouse), Accession No. Q9EPS3, Database EBI [Online] (Mar. 2001).

D–glucuronyl C5–epimerase (EC 5.1.3.–) amino acid sequence (bovine), Accession No. O18756, Database EBI [Online] (Jan. 1998).

Database Biosis Bioscience Information Service, Database accession no. PREV20000122890, abstract for Hagner–McWhirter, A. et al., "Biosysnthesis of heparin/heparan sulphate: Kinetic studies of the glucuronyl C5–epimerase with N–sulfated derivatives of the *Escherichia coli* K5 capsular polysaccharide as substrates," (Feb. 2000).

D–glucuronyl C5–epimerase amino acid sequence (EC 5.1.3.–), Accession No. O94923, Database EBI [Online] (May 1999).

Dialog File 351, Accession No. 2001–381292/200140, Derwent WPI English language abstract for WO 01/38507 (May 31, 2001).

International Search Report for International Application No. PCT/FI01/01068 mailed on Dec. 9, 2002.

* cited by examiner

Fig. 1

TGGTTGTCCTGGAACTCACTCTGTAGACCAGGCTGGCCATGAACTCACAGA
GATCTACCTCCTGAGTGCTGGGATTAAAGGTTTGTGCCACCACCTCCCAAC
TCTAAGGTGTTTCTTTAAGTTAGGGGCATAGTAAACATTGTTGAGATACTA
GAGGAACACTGAATGAAAATTTGGACATCTCTGCTTTAGGTTTGTGCTGAG
CAGTTTGCCTCTTATCTTCACCTATGCTGAAAGTTTGAGTTCATAATTTTG
AACATGCATATGATAAAATATTCTGGCCGCACATTGAATAAATATATTTTAA
ATGAACTTACCTTTAAAATGTCAGTAACAACTCTGCATGGTTTTCTTCTTAC
CTCCATAGGTATGGTCTGAAT<u>ATGCGTTGTTTGGCAGCTCGGGTCAACTAT</u>
<u>AAGACTTTGATTATCATCTGTGCGCTATTCACTTTGGTCACAGTACTTTTGT</u>
<u>GGAATAAGTGTTCCAGCGACAAAGCAATCCAGTTTCCTCGGCACTTGAGTA</u>
<u>GTGGATTCAGAGTGGATGGATTAGAAAAAGATCAGCAGCATCTGAAAGTA</u>
<u>ACCACTATGCCAACCACATAGCCAAACAGCAGTCAGAAGAGGCATTTCCTC</u>
<u>AGGAACAACAGAAGGCACCCCCTGTTGTTGGGGGCTTCAATAGCAACGGG</u>
<u>GGAAGCAAGGTGTTAGGGCTCAAATATGAAGAGATTGACTGTCTCATAAAC</u>
<u>GATGAGCACACCATTAAAGGGAGACGAGAGGGGAATGAAGTTTTCCTTCCA</u>
<u>TTCACTTGGGTAGAGAAATACTTTGATGTTTATGGAAAAGTGGTCCGAGTA</u>
<u>TGACGGCTATGATCGATTTGAATTC::TCTCATAGCTATTCCAAAGTCTATGCA</u>
<u>CAGAGAGCCCCTTATCACCCTGATGGTGTGTTTATGTCCTTTGAAGGCTACAATG</u>
<u>TGGAAGTCCGAGACAGAGTCAAGTGCATAAGTGGGGTTGAAGGTGTACCTTTAT</u>
<u>CTACACAGTGGGGACCTCAAGGCTATTTCTACCCAATCCAGATTGCACAGTATG</u>
<u>GGTTAAGTCACTACAGCAAGAATCTAACTGAAAAACCCCCTCATATAGAGGTAT</u>
<u>ATGAAACAGCAGAAGACAGGGACAAAAACAGCAAGCCCAATGACTGGACTGTG</u>
<u>CCCAAGGGCTGCTTTATGGCTAGTGTGGCTGATAAGTCAAGATTCACCAATGTT</u>
<u>AAACAGTTCATTGCTCCAGAAACCAGTGAAGGTGTATCCTTGCAACTGGGGAAC</u>
<u>ACAAAAGATTTTATTATTTCATTTGACCTCAAGTTCTTAACAAATGGAAGCGTGT</u>
<u>CTGTGGTTCTGGAGACGACAGAAAAGAATCAGCTCTTCACTGTACATTATGTCT</u>
<u>CAAATACCCAGCTAATTGCTTTTAAAGAAAGAGACATATACTATGGCATCGGGC</u>
<u>CCAGAACATCATGGAGCACAGTTACCCGGGACCTGGTCACTGACCTCAGGAAA</u>
<u>GGAGTGGGTCTTTCCAACACAAAAGCTGTCAAGCCAACAAGAATAATGCCCAA</u>

```
GAAGGTGGTTAGGTTGATTGCGAAAGGGAAGGGCTTCCTTGACAACATTACCAT
CTCTACCACAGCCCACATGGCTGCCTTCTTCGCTGCCAGTGACTGGCTGGTGAG
GAACCAGGATGAGAAAGGCGGCTGGCCGATTATGGTGACCCGTAAGTTAGGGG
AAGGCTTCAAGTCTTTAGAGCCAGGGTGGTACTCCGCCATGGCCCAAGGGCAAG
CCATTTCTACATTAGTCAGGGCCTATCTCTTAACAAAAGACCATATATTCCTCAA
TTCAGCTTTAAGGGCAACAGCCCCTTACAAGTTTCTGTCAGAGCAGCATGGAGT
CAAGGCTGTGTTTATGAATAAACATGACTGGTATGAAGAATATCCAACTACACC
TAGCTCTTTTGTTTTAAATGGCTTTATGTATTCTTTAATTGGGCTGTATGACTTAA
AAGAAACTGCAGGGGAAAAACTCGGGAAGAAGCGAGGTCCTTGTATGAGCGT
GGCATGGAATCCCTTAAAGCCATGCTCCCCTTGTACGACACTGGCTCAGGAACC
ATCTATGACCTCCGGCACTTCATGCTTGGCATTGCCCCAACCTGGCCCGCTGGG
ACTATCACACCACCCACATCAATCAACTGCAGCTGCTTAGCACCATTGATGAGT
CCCCAATCTTCAAAGAATTTGTCAAGAGGTGGAAGAGCTACCTTAAAGGCAGCC
GGGCAAAGCACAACTAG
```

FIGURE 1
CONTINUED

ATGCGTTGTTTGGCAGCTCGGGTCAACTATAAGACTTTGATTATCATCTGTGCGC
TATTCACTTTGGTCACAGTACTTTTGTGGAATAAGTGTTCCAGCGACAAAGCAAT
CCAGTTTCCTCGGCACTTGAGTAGTGGATTCAGAGTGGATGGATTAGAAAAAGA
TCAGCAGCATCTGAAAGTAACCACTATGCCAACCACATAGCCAAACAGCAGTCA
GAAGAGGCATTTCCTCAGGAACAACAGAAGGCACCCCCTGTTGTTGGGGGCTTCA
ATAGCAACGGGGGAAGCAAGGTGTTAGGGCTCAAATATGAAGAGATTGACTGTC
TCATAAACGATGAGCACACCATTAAAGGGAGACGAGAGGGGAATGAAGTTTTCC
TTCCATTCACTTGGGTAGAGAAATACTTTGATGTTTATGGAAAAGTGGTCCAGTA
TGACGGCTATGATCGATTTGAATTCTCTCATAGCTATTCCAAAGTCTATGCACAG
AGATCACCTTATCACCCTGACGGTGTGTTTATGTCCTTTGAAGGCTACAATGTGG
AAGTCCGAGACAGAGTCAAATGTATAAGTGGAGTTGAAGGTGTGCCATTATCTAC
CCAGTGGGGGCCTCAAGGCTATTTCTACCCAATCCAGATTGCACAGTATGGGCTA
AGTCATTACAGCAAGAATCTAACCGAGAAACCCCCTCACATAGAAGTATATGAA
ACAGCAGAAGACAGGGACAGAAACATCAGACCTAATGAATGGACTGTGCCCAAG
GGGTGcttCATGGCCAGTGTGGCAGACAAGTCTAGATCCACCAATGTTAAACAGTT
TATTGCTCCAGAAACCAGTGAAGGTGTGTCTTTGCAGCTGGGAAACACAAAAGAC
TTCATTATTTCATTTGACCTCAAGCTTTTAACAAATGGGAGTGTGTCTGTGGTTCT
GGAGACCACAGAAAAGAATCAGCTCTTCACTGTGCATTATGTCTCAAACACCCAG
CTGATTGCTTTCAGAGACAGGGACATATACTACGGCATTGGGCCCAGAACTTCAT
GGAGTACAGTTACCAGAGACCTGGTCACTGACCTCAGGAAAGGAGTGGGCCTTT
CTAACACAAAAGCTGTCAAGCCAACCAAAATCATGCCCAAAAGGTGGTTAGGT
TGATTGCAAAAGGGAAGGGATTCCTGGACAACATTACCATCTCAACCACAGCCC
ACATGGCTGCATTCTTTGCTGCAAGTGACTGGCTAGTGAGGAACCAGGATGAGAA
AGGTGgctGGCCAATTATGGTGACCCGGAAGTTAGGGGAAGGGTTTAAATCTTTAG
AACCAGGATGGTACTCTGCCATGGCACAAGGGCAAGCCATCTCTACCTTAGTCAG
GGCCTATCTTCTAACGAAAGACTATGTATTCCTCAGTTCAGCTTTAAGGGCAACA
GCCCCATACAAGTTTCCGTCAGAGCAGCATGGAGTTAAAGCCGTGTTCATGAATA
AACATGACTGGTATGAAGAATATCCAACCACACCTAGCTCTTTTGTTTTAAATGG
CTTTATGTATTCTTTAATTGGGCTGTATGACCTAAAAGAAACAGCAGGGGAGACA

FIG. 2

```
CTTGGGAAAGAAGCAAGGTCCTTGTACGAGCGCGGCATGGAATCTCTTAAAGCC
ATGCTGCCCTTGTATGATACTGGCTCCGGGACCATCTATGACCTCCGCCACTTCA
TGCTTGGCATTGCTCCCAACCTGGCCCGCTGGGACTATCACACCACCCACATTAA
CCAGCTGCAGCTGCTCAGCACCATCGATGAGTCCCCAATCTTCAAAGAATTTGTC
AAGAGGTGGAAAAGCTACCTTAAAGGCAGTAGGGCAAAGCACAAC
```

FIG. 2 CONT'D

MetArgCysLeuAlaAlaArgValAsnTyrLysThrLeuIleIleIleCysAlaLeuPheThrLeuValThrValLe
uLeuTrpAsnLysCysSerSerAspLysAlaIleGlnPheProArgHisLeuSerSerGlyPheArgValAspGlyL
euGluLysArgSerAlaAlaSerGluSerAsnHisTyrAlaAsnHisIleAlaLysGlnGlnSerGluGluAlaPheP
roGlnGluGlnGlnLysAlaProProValValGlyGlyPheAsnSerAsnGlyGlySerLysValLeuGlyLeuLy
sTyrGluGluIleAspCysLeuIleAsnAspGluHisThrIleLysGlyArgArgGluGlyAsnGluValPheLeuP
roPheThrTrpValGluLysTyrPheAspValTyrGlyLysValValGlnTyrAspGlyTyrAspArgPheGluP
heSerHisSerTyrSerLysValTyrAlaGlnArgSerProTyrHisProAspGlyValPheMetSerPheGluGly
TyrAsnValGluValArgAspArgValLysCysIleSerGlyValGluGlyValProLeuSerThrGlnTrpGlyPr
oGlnGlyTyrPheTyrProIleGlnIleAlaGlnTyrGlyLeuSerHisTyrSerLysAsnLeuThrGluLysProPro
HisIleGluValTyrGluThrAlaGluAspArgAspArgAsnIleArgProAsnGluTrpThrValProLysGlyC
ysPheMetAlaSerValAlaAspLysSerArgSerThrAsnValLysGlnPheIleAlaProGluThrSerGluGly
ValSerLeuGlnLeuGlyAsnThrLysAspPheIleIleSerPheAspLeuLysLeuLeuThrAsnGlySerValSe
rValValLeuGluThrThrGluLysAsnGlnLeuPheThrValHisTyrValSerAsnThrGlnLeuIleAlaPhe
ArgAspArgAspIleTyrTyrGlyIleGlyProArgThrSerTrpSerThrValThrArgAspLeuValThrAspLe
uArgLysGlyValGlyLeuSerAsnThrLysAlaValLysProThrLysIleMetProLysLysValValArgLeuIl
eAlaLysGlyLysGlyPheLeuAspAsnIleThrIleSerThrThrAlaHisMetAlaAlaPhePheAlaAlaSerA
spTrpLeuValArgAsnGlnAspGluLysGlyGlyTrpProIleMetValThrArgLysLeuGlyGluGlyPheLy
sSerLeuGluProGlyTrpTyrSerAlaMetAlaGlnGlyGlnAlaIleSerThrLeuValArgAlaTyrLeuLeuT
hrLysAspTyrValPheLeuSerSerAlaLeuArgAlaThrAlaProTyrLysPheProSerGluGlnHisGlyVal
LysAlaValPheMetAsnLysHisAspTrpTyrGluGluTyrProThrThrProSerSerPheValLeuAsnGlyP
heMetTyrSerLeuIleGlyLeuTyrAspLeuLysGluThrAlaGlyGluThrLeuGlyLysGluAlaArgSerLe
uTyrGluArgGlyMetGluSerLeuLysAlaMetLeuProLeuTyrAspThrGlySerGlyThrIleTyrAspLeu
ArgHisPheMetLeuGlyIleAlaProAsnLeuAlaArgTrpAspTyrHisThrThrHisIleAsnGlnLeuGlnLe
uLeuSerThrIleAspGluSerProIlePheLysGluPheValLysArgTrpLysSerTyrLeuLysGlySerArgAl
aLysHisAsn

FIG. 3

```
SCORE      ▬ ▬▬   ▬      ▬▬▬       ▬▬▬  ▬                          ▬▬ ▬▬▬▬
mouse liver...    1 M------R-CLAA-------------------------------------RVNYKILIIC-ALFTLVTVL-L
bovine lung       1 ---------------------------------------------------------------------
human EST ho...   1 ---------------------------------------------NYKILIIIC-ALFTIVTVL-L
Drosophila        1 MSKYLSSQRDAISAP-----AL-PVS-----RENREPPKFQGVKQREPLVFFIMRINIKAVLIVL_TVAVVITLGV
C. elegans h...   1 MV--LVSLK-----PFNLFSILKEMKCIRWRSNR----------HR-----IY-------LIVACGALFLL
Methanococcu..   1 MI-----------L---------MK----------------------KFE---------IIIFLF-----IAVLIFVFG- SCORE             ▬▬    ▬▬▬      ▬▬                                    ▬▬▬▬▬
mouse liver...   81 SDKAIQFPRHLSSGF-R-VDGIEKRSAASE-SNHYANFLAKQQSEEAFPQ-----EQQKA----PPVVGGENSNVGS
bovine lung      33 ---------------------------------------------------------------------
human EST ho...   1 ---------------------------------------------------------------------
Drosophila       25 SDKAIQFPRRSSSGF-R-VDGFEKRAAASESNNYMNHVAKQQSEEAFPQ-----EQQKA----PPVVGGENSNVGS
C. elegans h...  71 ---AFSF-----SPDFVRPID----RSA----------RQS-------------------------SSGGE
Methanococcu..   43 ---------RHLTQ-------E-----ES-----RI-DEEDEE-LIQVDNEDKKIECEPP-----GSIES-
                 25 ---------------FV---------GASQF-LY-------------SE------N-----------PVI SCORE                ▬▬▬  ▬  ▬                   ▬▬                     ▬▬▬▬▬▬
mouse liver...  161 KVEEIDCLINDE-HTIKGRRE---GNEVFLPFIWEEKFDVIGKV------VQIDGYDREFSHSYSKVYAQRSP
bovine lung       1 ----------------------------------------------------------SHSYSKVYAQRAP-
human EST ho... 103 KVEEIDCLINDE-HTIKGRRE---GNEVFLPFIWVEKFDVIGKV------VQIDGYDREFSHSYSKVYAQRAP-
Drosophila       95 HDIECSINQE-YTVHCKRDENANEVYVPFSEFLRNIFDVSGAVSTNSNEVA----KENWMHSTAKVNLFRGK
C. elegans h..   99 K------CIADNG-KSMKCWKDE-EDVYFPVSYLKKRFDMIGKLGK--------DG-STFELYTSAKM---RSED
Methanococcu..   82 QY-------FKNEKPFIV------EN----VNMEVTY----YGTIICEK-------------YIGY-----------QITP-
                 40
```

FIG. 4A

| | | |
|---|---|---|
| SCORE | 241 | |
| mouse liver ... | 171 | DGVEMSFEGINV--EVRDRVKCISGVEGVPLSTQWGRGYFYPTQIAQYGLSHYSK--------NLIEKPHIEVY |
| bovine lung | 17 | DGVEMSFEGINV--EVRDRVKCISGVEGVPLSTQWGRGYFYPTQIAQYGLSHYSK--------NLIEKPHIEVY |
| human EST ho... | 163 | DGVEMSFEGINV--EVRDRVKCISGVEGVPLSTQWGRGYFYPTQIAQYGLSHYSK--------NLIEKPHIEVY |
| Drosophila | 168 | RGVIMYFENINV--EVRDRVKCISAAEGVPVSIQWEKRGYFYPTQIAQEALSHYSK--------NLIEPAPRVRVL |
| C. elegans h... | 143 | LGPFGHFSTYSV--ETFDRVRCVSPAKIDVEMSIQADPIPYYYPTQISQDYGLQHVSRMKLDSINKSEASPKDDVI |
| Methanococcu... | 75 | ---------------HNVNEEAR---KC-------------FYK-------YFKLK |

| | | |
|---|---|---|
| SCORE | 321 | |
| mouse liver ... | 242 | RDRNITRPNEW--------T-VPKGCF----MASVADKSRSTNVKQFTAPETS----EGV-SLQIGNIKDF-IISFD |
| bovine lung | 88 | RDRNSKPNDW--------T-VPKGCF----MASVADKSRFTNVKQFTAPETS----EGV-SLQIGNIKDF-IISFD |
| human EST ho... | 234 | RDKN-KPNDW--------T-VPKGCF----MANVADKSRFTNVKQFTAPETS----EGV-SLQIGNIKDF-IISFD |
| Drosophila | 236 | GDQKQM-EW---------S-TPKDSN----MIRIWHHKENTSVVQF--------ETAPGEGVLSIAINQITIDL-LLSVD |
| C. elegans h... | 219 | ----NSK--EMKGAAQMHET-TERLEFNDEQMGKV-------VNLSAGAALANAGAY--------VYLDKSPDLHVISFD |
| Methanococcu... | 93 | -DKN--PKE----A---ERYIKRGLFLTEYLLISQADK------------ETA |

| | | |
|---|---|---|
| SCORE | 401 | |
| mouse liver ... | 304 | NGS---VSVVLETEKNQLFTVHYV-----------SNTQLIAF--REDIYYG----IG--PRTSWSTVT |
| bovine lung | 150 | NGS---VSVVLETEKNQLFTVHYV-----------SNTQLIAF--KERDIYYG---IG--PRTSWSTVT |
| human EST ho... | 295 | NGS---VSVVLETEKNQLFTIHYV-----------SNAQLIAF--KERDIYYG---IG--PRTSWSTVT |
| Drosophila | 297 | NSSSIMITVQNFDTRHN--YSLHYI-----------PADILLSV--QDINIYYG----LGGSALNKWRHIT |
| C. elegans h... | 282 | ANSSF--TVLARMKQDILVLINYYSEGNGKCVWQEEERISDDYIVQEEKDGQVSYSYIQNSPIGEWSTVT |
| Methanococcu... | 123 | ---------EVDEKN---IIFI-----VW----R----------------YNFEF--P------ |

FIG. 4B

```
SCORE            481 ▇▇▇ ▄▃▂ ▃▂ ▂  ▃▂▂▃▃▂▂▃▂▃▂▂▃▃▂▂▂▃▃▂▂▂▃▂▂▃▂▂▂▂▃▂▂▃▂▂▂▃▂▂▃▂▂▂▂▂▂▂▂▂▂▂▂▂▂▂▂▂▂▂▂▂▂▂▂▂▂▂▂▂▂▂▂▂▂▂▂
mouse liver...   358 DLRKGVGLS---NTKAVKPTKIMPKK-----VVRLIARGKGFL---DNITISTAHMAAFFAASDWLVRNQDEK-G
bovine lung      204 DLRKGVGLS---NTKAVKPTKIMPKK-----VVRLIARGKGFL---DNITISTAHMAAFFAASDWLVRNQDEK-G
human EST ho...  349 DLRKGVGLS---NTKAVKPTKIMPKK-----VVRLIARGKGFL---DNITISTAHMAAFFAASDWLVRNQDEK-G
Drosophila       354 DLQRGI-MG---DKRS--PLKI--RRSDLEVISIGFLGLGFF---DNITLSTSDHLAHFTDAAEWFVENQDPKTG
C. elegans h...  360 DVAR--ALSSGDNRR--KDDNVLHAGDLRLVSLGFRGE--LTVQXITQRREQHSHAFTAAADWLVRNQNDR-G
Methanococcu..   144 NLSRG----------

SCORE            561 ▇▇▇ ▄▃▂▃▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂
mouse liver...   425 IMVTRKLGEGFKSLEPGWYSAMAQCQAISTLVRAYLLIK----DTVFLSSALRAYA----PYTKFPSEQHGVKAV---
bovine lung      271 IMVTRKLGEGFKSLEPGWYSAMAQCQAISTLVRAYLLIK----DHIFLNSALRAYA----PYTKELSEQHGVKAV---
human EST ho...  416 IMVTRKLGEGFKSLEPGWYSAMAQCQAISTLVRAYLLIK----DHIFLNSALRAYA----PYTKELSEQHGVKAV---
Drosophila       423 --VRRSIN--GFAELRPGWISAMEQCHAISVLAPAYWHSG--GDERYL---RAAAAGLQPTRVYSRDGGVLAQ---
C. elegans h...  433 --VERSIAERKIVLPPGWHSAMAQGHGISVLTRAF--KHENDEKYLKSAAKA---LKLFINSSDGGVRGE---
Methanococcu..   149 ----------------WRGALCQAGCLKTLYIAYEAT----GDERYINYANLAYIDA-----FKVFVERGGLIKTRI SCORE            641 ▇▇▇ ▄▃▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂
mouse liver...   495 HDWTEEYPTTPSSFVLNGEMYSLIGLYDLK---------ETAGEKLGEARSLYERGMESLRAMLPLYDTGSGT
bovine lung      341 HDWTEEYPTTPSSFVLNGEMYSLIGLYDLK---------ETAGEKLGEARSLYERGMESLRAMLPLYDTGSGT
human EST ho...  486 HDWTEEYPTTPSSFVLNGEMYSLIGLYDLK---------ETAGEKLGEARSLYERGMESLRAMLPLYDTGSGT
Drosophila       491 FYWTEEYPTTPSYVLNGFLYSILGLYDIN------------STAPGKIAERAGKLFAQGMHSLRKMLLLFDTGSGT
C. elegans h...  501 I-WTEEYPTTPGSFVLNGFLYSLIGLYDLSQLEIMDENDETMRAKI-QKAQFLYSAGVRSLKQLLPLYDTGSGT
Methanococcu..   205 YIWMFFYASENPPYVLNGFI----------

SCORE            721 ▇▇▇ ▄▃▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂▂
mouse liver...   565 HEMLGIAPNLARGDYHTTHINQLQLLSTIDESPIFKEFVKRGKSYLKGSRAKHN
bovine lung      411 HEMLGIAPNLARGDYHTTHINQLQLLSTIDESPIFKEFVKRGKSYLKGSRAKHN
human EST ho...  556 HEMLGIAPNLARGDYHTTHINQLQLLSTIDESPIFKEFVKRGKSYLKGSRAKHN
Drosophila       561 HLSLGVAPNLARGDYHATHVNQLLLLATIDSDPLIAQTAERGKGYMEGRRAKHN
C. elegans h...  579 HVALGTAPNLARGDYHAVHVYLLKWIAGTEKDEVLSKIADRWIGYAYGKRAKHN
Methanococcu..   225 --------------
```

First active tagged recombinant (bovine) C5
(specific activity 5 X 10^5 cpm/mg/h)

bovine

The most active recombinant (full mouse) C5
(specific activity 2 X 10^5 cpm/mg/h)

Chimeric construct
(preliminary data indicate activity is 87% of full mouse):

mouse          bovine

Truncated mouse
(preliminary data indicate activity is same as first bovine construct):

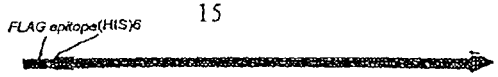

FIG. 6B

```
       EGT signal peptide                              FLAG epitope                     Enterokinase cleavage site                (HIS)6
                                                      EGT signal cleavage
 ATGACTATTCTCTGCTGGCTTGCGCTGTTGTCAACACTTACCGCCGTCAACACACT ACAAGGACGACGATGAC AACGGCCGCATGCGGAATTCATGCGGGGTTCTCATCACCAT
 MetThrIleLeuCysTrpLeuAlaLeuLeuSerThrLeuThrAlaValAsnAlaAspTyrLysAspAspAspAspLysArgProHisAlaGluPheMetArgGlySerHisHisHis
                                                                    (TEV protease site)
 CACCATCACGATTACGATATCCCAACGACCGAAAAACCTGTATTTTCAGGGCGCCATG
 HisHisHisAspTyrAspIleProThrThrGluAsnLeuTyrPheGlnGlyAlaMet
```

GLUCURONYL C5-EPIMERASE, DNA ENCODING THE SAME AND USES THEREOF

CROSS-REFERENCE TO RELATED APPLICATIONS

This application claims the benefit of provisional U.S. application No. 60/304,180, which was converted from U.S. application Ser. No. 09/732,026 filed Dec. 8, 2000, the contents of which are incorporated herein by reference.

STATEMENT REGARDING FEDERALLY-SPONSORED RESEARCH AND DEVELOPMENT

Not applicable.

FIELD OF THE INVENTION

The invention is in the field of recombinant proteins, and especially, glucuronyl C5-epimerases and the use of the same for the modification of glucosaminoglycans.

BACKGROUND OF THE INVENTION

Glucuronyl C5-epimerase (herein, "C5-epimerase") catalyzes the conversion of D-glucuronic acid (GlcA) to L-iduronic acid (IdoA) in the second polymer modification step of heparin/heparan sulfate (HS) synthesis. The epimerase involved in heparin/HS synthesis has an absolute requirement for N-sulfate at the nonreducing side of the target HexA, the formation of which is catalyzed by a N-Deacetylase-N-sulfotransferase (NDST) in the first (preceding) step of biosynthetic polymer modification. Also, the epimerase is inhibited by O-sulfate groups near its site of action, so O-sulfation steps later in the heparin biosynthetic pathway inhibit epimerization or back-epimerization. The reaction involves reversible abstraction and readdition of a proton at C5 of the target hexuronic acid, via carbanion intermediate, and is believed to involve two polyprotic basic amino acids (esp. Lys).

The C5-epimerase, like other enzymes involved in heparin/HS biosynthesis, appears to be membrane bound or associated in the Golgi. Interestingly, solubilized epimerase catalyzes both (reversible) reactions, but no back-epimerization is detectable from microsomal fractions. C5-epimerase active protein was first purified and characterized from liver (Campbell et al., *J. Biol. Chem.* 269:26953–26958 (1994)).

Campbell, P. et al., reported the purification of the D-glucuronyl C5-epimerase from bovine liver (Campbell et al., *J. Biol. Chem.* 269: 26953–26958 (1994)), and several DNA sequences have also been reported. While the predicted size of the bovine C5-epimerase from genomic and cDNA sequences is 70.1 KD (618 amino acids) (discussed below), the most purified native preparate extracted as above contained predominant species of 52 and 20 kDa, indicating that proteolytic cleavage (processing) may have occurred. Detection of activity in larger MW (200 kDa) fractions from size-exclusion chromatography indicated that aggregation or oligomerization may occur. The enzyme has a broad pH range (6.5–7.5) of activity, having an optimum 7.4. The enzyme does not have a metal ion or other cofactor requirement. Kinetic studies unexpectedly revealed that the $K_m$ increases with increasing enzyme concentration, probably relating to polymeric substrate and stearic hindrance, and/or oligomerization of the epimerase molecules.

Recently, Lindahl, U. and Li, J-P., WO98/48006, purified the 52 kDa C5-epimerase from bovine liver and obtained a partial amino acid sequence. Primers were made against an internal sequence and used to amplify a sequence from a bovine liver cDNA preparation. The bovine liver sequence was used to screen a bovine lung cDNA library. A sequence having an open reading frame of 444 amino acids was found, which corresponded to a polypeptide of 49.9 kDa. It was stated that the enzyme previously isolated from bovine liver was a truncated form of the native protein. Total RNA from bovine liver, lung and mouse mastocytoma were analyzed by hybridization to the bovine lung epimerase cDNA clone. Both bovine liver and bovine lung gave identical results, with a dominant transcript of about 9 kb and a weak 5 kb band. The mouse mastocytoma RNA only showed the transcript at about 5 kb.

The report of the cloning of a cDNA encoding a C5-epimerase from bovine lung also appeared in Li et al. *J. Biol. Chem.* 272: 28158–28163 (1997). Li et al. cloned and expressed the bovine lung epimerase in a baculovirus/insect cell system, which first assigned activity to a cloned (recombinant) sequence. The active recombinant protein was not purified for definitive assignment.

C5-epimerase cDNA sequences from *Drosophila* (GenBank Accession Number AAF57373), *C. elegans* (GenBank Accession Number P46555) and *Methanococcus* (GenBank Accession Number U67555) have been reported.

The enzymatic activity of the recombinant bovine epimerase reported by Lindahl et al. was relatively low. However, attempts to express the bovine lung C5-epimerase, the sole cloned mammalian epimerase, in systems that might yield a better production failed. Expression in mammalian cells, *Saccharomyces cerevisiae*, and *E. coli* have been attempted. To date, there have been no reports of the successful production of a soluble, active C5-epimerase. Therefore, it has not been possible to expand the early baculovirus cell system results into other recombinant systems or to use conventional expression methods such as mammalian, yeast and bacterial systems for expression of this enzyme.

Thus, there remains a need in the art for a highly active C5-epimerase, and for methods for production of larger amounts of the same.

SUMMARY OF THE INVENTION

Recognizing that problems of an undefined nature exist with expressing recombinant epimerases of mammalian origin, and cognizant of the need for a useful method for expressing and producing useful amounts of the C5-epimerase, the inventors investigated recombinant C5-epimerase production methods. The studies culminated in the discovery of a novel mouse gene, and the mouse C5-epimerase protein encoded therein. The mouse C5-epimerase of the invention is unique, inter alia, in that it contains additional sequences at its N-terminus in comparison to the C5-epimerase protein sequences known in the art. It has been unexpectedly discovered that the fusion of the mouse C5-epimerase's N-terminal fragment, or shortened versions thereof, to the N-terminus of other C5-epimerases, greatly enhances the activity of those other recombinant C5-epimerase activity by orders of magnitude. Thus the mouse N-terminus extension can be used to facilitate expression of sequences that are operably linked to it, and especially, expression of native (murine liver) and heterologous (both non-murine and murine non-hepatic) forms of C5-epimerases in recombinant systems.

Accordingly, in a first embodiment, the invention is directed to purified and/or isolated polynucleotides encoding a mouse (murine) liver C5-epimerase, and recombinant vectors and hosts for the maintenance and expression of the same.

In a further embodiment, the invention is directed to the purified and/or isolated mouse liver C5-epimerase protein encoded by such polynucleotides, or preparations containing the same.

In a further embodiment, the invention is directed to methods of producing the mouse C5-epimerase using such polynucleotides and the recombinant vectors and hosts of the invention to express the same.

In a further embodiment, the invention is directed to polynucleotides, especially purified and/or isolated polynucleotides, encoding a fusion protein, such fusion protein containing the N-terminal sequence of the mouse C5-epimerase, operably linked in-frame to the amino acid sequence of a desired protein, and especially, a heterologous C5-epimerase sequence, and vectors and hosts for the maintenance and expression of such polynucleotides.

In a further embodiment, the invention is directed to the purified and/or isolated C5-epimerase fusion protein encoded by such polynucleotides.

In a further embodiment, the invention is directed to methods of producing a desired protein, by operably linking a polynucleotide that encodes the mouse C5-epimerase, or its N-terminal sequence, to a polynucleotide that encodes such desired protein of interest, and expressing the same in a recombinant host of the invention.

In a further embodiment, the invention is directed to polynucleotide sequences and vectors that provide polynucleotides encoding the N-terminal fragment polynucleotide sequence of mouse C5-epimerase, such polynucleotides and vectors having desired restriction sites at the 3'-terminus of the fragment for insertion (linkage) of a desired sequence thereto, especially, a sequence that encodes a protein of interest, and most especially, another epimerase sequence.

In a further embodiment, the invention is directed to methods of using the N-terminal sequence of mouse C5-epimerase for the expression of native and heterologous sequences linked thereto.

BRIEF DESCRIPTION OF THE FIGURES

FIG. 1. DNA sequence (SEQ ID No. 3) of a fusion protein having the sequence of the bovine C5-epimerase (non-bold—the entire sequence after the two colons in line 17) and the N-terminus of the mouse C5-epimerase (bold—the entire sequence before the two colons in line 17). The open reading frame (ORF) showing the polypeptide coding sequence is underlined.

FIG. 2. The complete DNA sequence of mouse C5-epimerase (SEQ ID No. 1).

FIG. 3. The complete amino acid sequence of mouse C5-epimerase (SEQ ID No. 2).

FIGS. 4(A–C). Alignment analysis of mouse C5-epimerase to other sequences showing regions of homology. The scores are shown on the top line and are listed in the column after the source of the sequence. The sequences are taken from the following sources: line 2: mouse liver (SEQ ID No. 4); line 3: bovine lung (SEQ ID No. 5); line 4: human EST (SEQ ID No. 6); line 5: Drosophila (SEQ ID No. 7); line 6: C. elegans (SEQ ID No. 8); line 7: Methanococcus (SEQ ID No. 9).

FIGS. 6A–6B. FIG. 6A: Diagrammatic representations of the products of the tagged recombinant (bovine) C5-epimerase constructions. i: First active tagged recombinant (bovine) C5-epimerase construct. The specific activity was $5 \times 10^5$ cpm/mg/h). ii: The most active recombinant (full mouse) C5 construction. The specific activity was $2 \times 10^9$ cpm/mg/h. iii: Chimeric construct having both mouse and bovine sequences. The activity was 87% of the activity of the full-length mouse sequence. iv: Truncated mouse construct. The activity is the same as the bovine construct in "i". FIG. 6B: sequence (SEQ ID No. 10) and domain information of the tag that preceded each of the recombinant constructs in FIG. 6A.

DETAILED DESCRIPTION OF THE PREFERRED EMBODIMENTS

Figure 5:
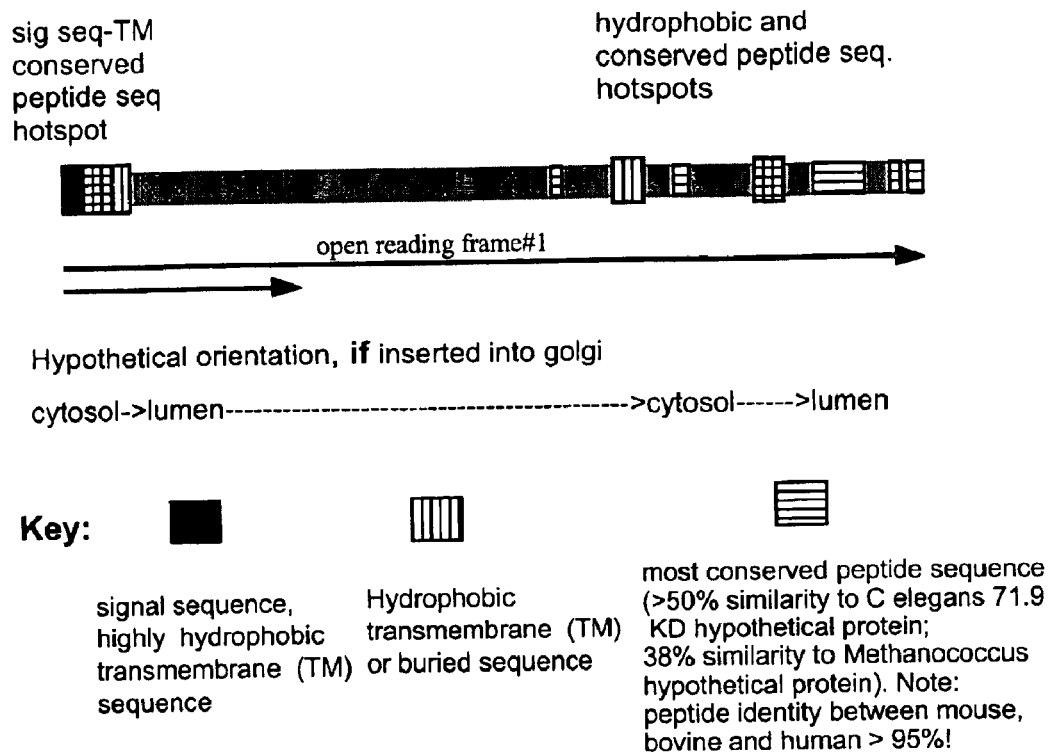
FIG. 5. Diagrammatic representation of the domain structure of the mouse C5-epimerase (SEQ ID No. 2). Solid rectangular box at the N-terminus: signal sequence (highly hydrophobic transmembrane (TM) sequence); hatched rectangular boxes: hydrophobic transmembrane (TM) or buried sequences; solid rectangular boxes within the peptide: conserved peptide sequences having greater than 50% similarity to the C. elegans 71.9 KD hypothetical protein.

A mouse liver gene encoding C5-epimerase was cloned. The nucleotide sequence is shown in FIG. 2. The amino acid sequence of the mouse liver C5-epimerase protein was found to be 618 amino acids long (FIG. 3), with a molecular weight of 71,180.1 daltons (71.18 kDa). The mouse C5-epimerase has an isoelectric point of 8.25 and a net charge at pH 7 of +4.01.

The amino acid sequence of the mouse liver C5-epimerase sequence, without any N-terminal extension is homologous (>96% amino acid identity) to the bovine C5-epimerase sequence. However, sequence analysis revealed that the N-terminus of the enzyme that is encoded by the mouse genomic sequence contained an additional 154 amino acids (amino acid) that were "missing" from the cloned bovine sequence.

The mouse coding sequence displayed >95% peptide identity to the corresponding bovine and human (expressed sequence tag from brain cDNA library) sequences, >50% similarity to a hypothetical 71.9 kDa protein from expressed sequence of C. elegans, and 38% similarity to a protein from an expressed sequence of Methanococcus sp.

The predicted transmembrane topology (hydrophobicity plot) of the mouse C5-epimerase enzyme resembles that of NDST. These and other observations (e.g., speed of heparin synthesis) indicated that the C5-epimerase and other enzymes of heparin biosynthesis are likely associated in a complex in vivo.

The recombinant mouse C5-epimerase, as expressed and secreted by an insect cell signal, from the baculovirus insect cell system, is most stable in medium at 4° C. Purification of the recombinant C5-epimerase may include, but is not limited to, such processes as cation exchange or affinity chromatography. For example, the recombinant protein may be engineered such that the protein contains a FLAG-tag or His-tag that occurs at either end of the recombinant protein. As one of ordinary skill in the art will appreciate, in such instances, the recombinant protein may be purified using commercially available resins which utilize, for example, anti-FLAG monoclonal antibodies to capture the recombinant protein comprising the FLAG epitome.

The enzyme is most rapidly assayed by biphasic extraction of tritium released from C5-labeled substrate into an organic scintillation cocktail, and counting, though ultimate confirmation of activity is by NMR analysis of converted product as described in the examples.

The native mouse liver enzyme has a specific activity of $5-10 \times 10^9$ cpm/mg/h, while that of the recombinant form of the mouse enzyme was about $2 \times 10^9$ cpm/mg/h. By comparison, the recombinant bovine enzyme has a specific activity of about $0.5-1.0 \times 10^6$ cpm/mg/h. Therefore, the recombinant mouse enzyme is an especially active C5-epimerase.

Unexpectedly, it was found that the 154 amino acid (amino acid) N-terminus of the mouse C5-epimerase, and especially certain fragments thereof, have the ability of being greatly able to enhance the enzymatic C5-epimerase activity of other C5-epimerases when fused in-frame to the N-terminus of the same. This additional 154 amino acid (amino acid) fragment appears to have at least three features that are desirable for the recombinant expression and secretion of an active C5-epimerase. First, it includes a sequence that is thought to function as a signal sequence comprised of the first 33–34 residues (amino acids 1–33 or 1–34 of FIG. 3). Second, it provides additional cysteine residues that are amenable for the formation of disulfide bonds and for the stabilization of secondary protein structure. Third, it provides an amidation site that is consistent with a site useful for posttranslational proteolytic processing.

Fragments of the 154 amino acid sequence that lack the signal sequence still possess the ability to enhance the activity of heterologous epimerases, and especially C5-epimerases, to which they are operably linked. For example, as shown in the examples, a fusion protein that contains amino acids 34–154 directly linked, in-frame to the N-terminus of the bovine C5-epimerase enhanced the activity of the bovine C5-epimerase over 100-fold.

Nucleic Acid Molecules

Accordingly, the invention is also directed to a method of increasing the activity of a C5-epimerase, the method comprising: providing a first polynucleotide comprising a nucleotide sequence encoding a polypeptide, the amino acid sequence of which is at least 80% identical to a reference amino acid sequence selected from the group consisting of amino acids 35 to 154 of FIG. 3 and amino acids 34 to 154 of FIG. 3; attaching said first polynucleotide of (a) to a second polynucleotide encoding a C5-epimerase; and expressing the fusion polynucleotide.

The present invention provides isolated nucleic acid molecules, comprising:
(1) a polynucleotide encoding the mouse liver C5-epimerase polypeptide having the amino acid sequence shown in FIG. 3.
(2) a polynucleotide encoding useful fragments of the mouse liver C5-epimerase polypeptide having the amino acid sequence shown in FIG. 3, such useful fragments including but not limited to (a) fragments that provide the signal sequence of amino acids 1–33 or 1–34; (b) fragments that provide the mature mouse liver C5-epimerase protein sequence, and especially amino acids 33–618 or 34–618, and (c) fragments that provide the sequence of the activity-stimulating N-terminus fragment having amino acids 1–154, and including fragments thereof such as amino acids 33–154 or 34–154 that possess the ability to enhance the activity of other C5-epimerases to which they are operably linked;

Unless otherwise indicated, all nucleotide sequences determined by sequencing a DNA molecule herein were determined as described in the examples, and all amino acid sequences of polypeptides encoded by DNA molecules determined herein were predicted by translation of a DNA sequence determined as above. Therefore, as is known in the art for any DNA sequence determined by this approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods which are well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

By "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U).

Using the information provided herein, such as the nucleotide sequence set out in Figures and sequence listing, a nucleic acid molecule of the present invention encoding a C5-epimerase polypeptide, or a chimeric construct of the same, may be obtained using standard cloning and screening procedures, such as those for cloning cDNAs using mRNA as starting material. Illustrative of the invention, the C5-epimerase nucleic acid molecule described in FIGS. 2 and 3 was discovered in a cDNA library derived from murine hepatic (liver) tissue.

The determined nucleotide sequence of the C5-epimerase DNA of FIG. 2 contains an open reading frame encoding a protein of about 618 amino acid residues, with an initiation codon at nucleotide position 1 of the nucleotide sequences in FIG. 2.

As one of ordinary skill would appreciate, due to the possibility of sequencing errors discussed above, the actual complete C5-epimerase polypeptide encoded by the sequence of FIG. 2, which comprise about 618 amino acids as shown in FIG. 3, may be somewhat longer or shorter. In any event, as discussed further below, the invention further provides polypeptides having various residues deleted from the N-terminus or the C-terminus of the complete polypeptide, including polypeptides lacking one or more amino acids from the N-terminus or C-terminus of the extracellular domain described herein.

The nucleic acid molecules of the invention include those that encode the C5-epimerase a signal sequence, as shown in FIG. 3, which is amino acids 1–33 or amino acids 1–34 of the amino acid sequence shown in FIG. 3. Such molecules can be operably linked in-frame to any desired nucleotide sequence, especially one that encodes a protein of interest that it is desired to secrete from a host in which the C5-epimerase signal sequence is capable of secreting.

Additionally, the nucleic acid molecules of the invention include those that encode the mouse liver C5-epimerase's "heterologous activity enhancing" sequence which is amino acids 1–154, or at least 30 amino acids thereof, as shown in FIG. 3. What is meant by the term "heterologous" nucleic acid is well known to one of ordinary skill in the art as being derived from the nucleic acid of a different species. Preferably, such nucleic acid molecules encode amino acids 1–154, 33–154 or 34–154 as shown in FIG. 3, plus or minus 1, 2, 3, 4, 5, 6, 7, 8, 9 or 10 amino acids from either or both ends. A nucleic acid encoding such a polypeptide can be operably linked, in frame, to the coding sequence for another epimerase, especially another C5-epimerases, with the result that a fusion protein is encoded by the nucleic acid construct. In a preferred embodiment, the heterologous activity enhancing sequences are expressed at the N-terminus of the fusion protein and are linked to the N-terminus of another protein whose activity is enhanced by the presence of the mouse sequence, most especially a non-mouse C5-epimerase or an isozyme of the mouse C5-epimerase.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA, or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) that encodes a C5-epimerase protein or fusion protein of the invention. DNA molecules comprising the coding sequence for the C5-epimerase protein as shown in FIG. 2, or desired fragment thereof; and DNA molecules which comprise a sequence substantially different from those described above, but which, due to the degeneracy of the genetic code, still encode the C5-epimerase protein amino acid sequence as shown in FIG. 3. Of course, the genetic code is well known in the art. Thus, it would be routine for one skilled in the art to generate such degenerate variants. In a further embodiment, nucleic acid molecules are provided that encode the C5-epimerase polypeptide as above, but lacking the N-terminal methionine, or the signal sequence encoded by amino acids 1–33 or 1–34 as shown on FIG. 3, or having the coding sequence of a different (heterologous) signal sequence operably linked thereto.

The invention further provides not only the nucleic acid molecules described above but also nucleic acid molecules having sequences complementary to the above sequences. Such isolated molecules, particularly DNA molecules, are usefull as probes for gene mapping, by in situ hybridization with chromosomes, and for detecting expression of the C5-epimerase gene in various species and tissues, for instance, by Northern blot analysis.

The present invention is further directed to fragments of the isolated nucleic acid molecules described herein that retain a desired property or that encode a polypeptide that retains a desired property or activity. By a fragment of an isolated nucleic acid molecule as described above is intended fragments at least about 15 nucleotides (nucleotide), and more preferably at least about 20 nucleotide, still more preferably at least about 30 nucleotide, and even more preferably, at least about 40 nucleotide in length which are useful as diagnostic probes and primers as discussed herein, or to provide a desired motif or domains to a fusion protein construct. Of course, larger fragments 50–300 nucleotide, or even 600 nucleotide in length are also useful according to the present invention as are fragments corresponding to most, if not all, of the nucleotide sequence of the DNA shown in FIG. 2 or encoding the amino acid sequence of FIG. 3. By a fragment at least 20 nucleotide in length when compared to that of FIG. 2, for example, is intended fragments which include 20 or more contiguous bases from the nucleotide sequence of the nucleotide sequence as shown in FIG. 2.

In particular, the invention provides polynucleotides having a nucleotide sequence representing the portion of that shown in FIG. 2 or encoding the amino acid sequence shown in FIG. 3. Also contemplated are polynucleotides encoding C5-epimerase polypeptides which lack an amino terminal methionine. Polypeptides encoded by such polynucleotides are also provided, such polypeptides comprising an amino acid sequence at positions 2 to 618 of the amino acid sequence shown on FIG. 3, but lacking an amino terminal methionine.

In another aspect, the invention provides an isolated nucleic acid molecule comprising a polynucleotide which hybridizes under stringent hybridization conditions to a portion or preferably all of the polynucleotide in a nucleic acid molecule of the invention described above. By a portion could be any desired portion, for example, the polynucleotide of FIG. 2 that encode amino acids 1–154 or 33–154 or 34–154. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5× Denhardt's solution, 10% dextran sulfate, and 20 μg/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nucleotide), and more preferably at least about 20 nucleotide, still more preferably at least about 30 nucleotide, and even more preferably about 30–70 (e.g., 50) nucleotide of the reference polynucleotide. These are useful as diagnostic probes and primers as discussed above and in more detail below.

By a portion of a polynucleotide of "at least 20 nucleotide in length," for example, is intended 20 or more contiguous nucleotides from the nucleotide sequence of the reference polynucleotide (e.g., the nucleotide sequence as shown in FIG. 2). Of course, a polynucleotide which hybridizes only to a poly A sequence, or to a complementary stretch of T (or U) residues, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention which encode a C5-epimerase polypeptide may include, but are not limited to the coding sequence for the polypeptide, by itself (also called the mature C5-epimerase when it lacks the secretion signal); the coding sequence for the polypeptide and additional sequences, such as those encoding a leader or secretary sequence, such as a pre-, or pro- or prepro- protein sequence; the coding sequence of the polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing—including splicing and polyadenylation signals, for example—ribosome binding and stability of mRNA; additional coding sequence which codes for additional amino acids, such as those which provide additional functionalities. Thus, for instance, the polypeptide may be fused to a marker sequence, such as a peptide, which facilitates purification of the fused (marker containing) polypeptide. In certain preferred embodiments of this aspect of the invention, the marker sequence is a hexa-histidine peptide, such as the tag provided in a pQE vector (Qiagen, Inc.), among others, many of which are commercially available. As described in Gentz et al., *Proc. Natl. Acad. Sci. USA* 86: 821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37:767–778(1984).

Variant and Mutant Polynucleotides

The present invention further relates to variants of the nucleic acid molecules of the present invention, which encode portions, analogs, or derivatives of the C5-epimerase. Variants may occur naturally, such as a natural allelic variant. By an "allelic variant" is intended one of several alternate forms of a gene occupying a given locus on a chromosome of an organism. *Genes II*, Lewin, B., ed., John Wiley & Sons, New York (1985). Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the C5-epimerase polypeptide or portions thereof. Also especially preferred in this regard are conservative substitutions.

Further embodiments of the invention include an isolated nucleic acid molecule comprising a polynucleotide having a nucleotide sequence encoding a polypeptide, the amino acid sequence of which is at least 80% identical to, and more preferably at least 90%, 95%, 96%, 97%, 98% or 99% identical to, a reference amino acid sequence selected from the group consisting of: (a) amino acids 1 to 118 of FIG. 3; (b) amino acids 1 to 119 of FIG. 3; (c) amino acids 1 to 120 of FIG. 3; (d) amino acids 1 to 121 of FIG. 3; (e) amino acids 119 to 618 of FIG. 3; (f) amino acids 120 to 618 of FIG. 3; (g) amino acids 121 to 618 of FIG. 3; (h) amino acids 122 to 618 of FIG. 3; (i) amino acids 34 to 147 of FIG. 3; (j) amino acids 35 to 154 of FIG. 3; (k) amino acids 34 to 154 of FIG. 3; and (l) amino acids 1 to 154 of FIG. 3; (m) the entire amino acid sequence shown on FIG. 3.

Further embodiments of the invention include isolated nucleic acid molecules that comprise a polynucleotide which hybridizes under stringent hybridization conditions to a polynucleotide in (a), (b), (c), (d), (e), (f), (g), (h), (i), (j), (k), (l), (m), (n), above. This polynucleotide which hybridizes does not hybridize under stringent hybridization conditions to a polynucleotide having a nucleotide sequence consisting of only A residues or of only T residues.

By a polynucleotide having a nucleotide sequence at least, for example, 95% "identical" to a reference nucleotide sequence encoding a C5-epimerase polypeptide is intended that the nucleotide sequence of the polynucleotide is identical to the reference sequence except that the polynucleotide sequence may include up to five point mutations per each 100 nucleotides of the reference nucleotide sequence encoding the C5-epimerase polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to, for instance, the nucleotide sequence shown in FIG. 2 can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2:482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 90%, 95%, 96%, 97%, 98% or 99% identical to a nucleic acid sequence shown in FIG. 2, irrespective of whether it encode a polypeptide having C5-epimerase activity. This is because even where a particular nucleic acid molecule does not encode a polypeptide having C5-epimerase activity, one of skill in the art would still know how to use the nucleic acid molecule, for instance, as a hybridization probe or a polymerase chain reaction (PCR) primer. Uses of the nucleic acid molecules of the present invention that do not encode a polypeptide having C5-epimerase activity include, inter alia: (1) isolating a C5-epimerase gene or allelic variants thereof in a cDNA library; (2) in situ hybridization (e.g., "FISH") to metaphase chromosomal spreads to provide precise chromosomal location of the C5-epimerase gene, as described in Verma et al., *Human Chromosomes: A Manual of Basic Techniques*, Pergamon Press, New York (1988); and Northern Blot analysis for detecting C5-epimerase mRNA expression in specific tissues.

Preferred, however, are nucleic acid molecules having sequences at least 90%, 95%, 96%, 97%, 98% or 99% identical to a nucleic acid sequence shown in FIG. 2 which does, in fact, encode a polypeptide having C5-epimerase activity. By "a polypeptide having C5-epimerase activity" is intended polypeptides exhibiting activity similar, but not necessarily identical, to an activity of the C5-epimerase of the invention (either the fall length protein or preferably the identified amino acid fragment containing amino acids 33–618 or 34–618), as measured in a particular biological assay.

Of course, due to the degeneracy of the genetic code, one of ordinary skill in the art will immediately recognize that a large number of the nucleic acid molecules having a sequence at least 80%, 90%, 95%, 96%, 97%, 98%, or 99% identical to the nucleic acid sequence of a deposited cDNA or the nucleic acid sequence shown in FIG. 2 will encode a polypeptide "having C5-epimerase protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having C5-epimerase protein activity. This is because the skilled artisan is fully aware of amino acid substitutions that are either less likely or not likely to significantly effect protein function (e.g., replacing one aliphatic amino acid with a second aliphatic amino acid), as further described below.

Vectors and Host Cells

The present invention also relates to vectors which include the isolated DNA molecules of the present invention, host cells which are genetically engineered with the recombinant vectors of the invention and the production of C5-epimerase polypeptides or fragments thereof by recombinant techniques.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the *E. coli* lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in *E. coli* and other bacteria. Representative examples of appropriate hosts include, but are not limited to, bacterial cells, such as *E. coli, Corynebacterium, Streptomyces* and *Salmonella typhimurium* cells; fungal cells, such as *Aspergillus, Aspergillus niger*, or *Trichoderma*, or yeast cells such as *Saccharomyces, Saccharomyces cerevisiae*; insect cells such as *Drosophila* S2 and *Spodoptera* Sf9 cells; animal cells such as CHO, COS and Bowes melanoma cells; and plant cells. Preferred hosts includes insect cells. Appropriate culture mediums and conditions for the above-described host cells are known in the art.

Among vectors preferred for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Viral vectors include, but are not limited to retroviral vectors, pox virus vectors, including vaccinia virus and adenoviral vectors. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

Polypeptides and Fragments

The invention further provides an isolated or purified C5-epimerase polypeptide having the amino acid sequences encoded by the amino acid sequences in FIG. 3, or a peptide or polypeptide comprising a portion of the above polypeptide, especially as described above and encoded by a nucleic acid molecule described above.

The invention further provides fusion proteins containing a functional portion of the N-terminus of the mouse C5-epimerase, fused at its C-terminus to the N-terminus of a protein of interest, such as, for example, the signal sequence of amino acids 1–33 or 1–34 as shown on FIG. 3, or the activity enhancing sequence of amino acids 1–154, 33–154 or 34–154 as shown on FIG. 3. In one embodiment, the protein of interest is fused to a portion of the N-terminus that contains from 30 to 154 amino acids of the N-terminus of mouse C5-epimerase of FIG. 3, and especially amino acids 33–154 or 34–154. In another preferred embodiment, the protein of interest is fused to a functional portion of the N-terminus that contains residues 33–154 of the sequence shown on FIG. 3. In a highly preferred embodiment, the protein of interest is fused to a functional portion of the N-terminus that contains the secretion signal of amino acids 1–33 or 1–34 as shown in the sequence on FIG. 3.

The polypeptide may be expressed in a modified form, such as a fusion protein, and may include not only secretion signals but also additional heterologous functional regions. What is meant by the term "heterologous" polypeptide is well known to one of ordinary skill in the art as being derived from different species. Thus, for instance, a region of additional amino acids, particularly charged amino acids, may be added to the N-terminus of the polypeptide to improve stability and persistence in the host cell, during purification or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art.

The C5-epimerase or fusion protein containing a fragment thereof can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or non-glycosylated. In addition, polypeptides of the invention may also include an initial modified methionine residue, in some cases as a result of host-mediated processes. The polypeptide of the instant invention may also include a modification of a histidine or poly histidine added to the termini for protein purification procedures.

C5-epimerase polynucleotides and polypeptides may be used in accordance with the present invention for a variety of applications, particularly those that make use of the chemical and biological properties of C5-epimerase. Specifically, the recombinant epimerases of the present invention may be used to produce heparin and/or heparan sulfate, which may be useful as anticoagulants, on a larger scale. Also, the epimerases of the present invention may be useful in an experimental setting for studying the effects of extracellular matrix molecules such as heparin and heparan sulfate on such processes as embryology, angiogenesis and tumor progression. For example, the enzyme can modulate the ratio of D-glucuronic acid/L-iduronic acid residues in heparin or heparan sulfate. L-iduronic acid residues, due to their unique conformational properties, are believed to promote interactions of polysaccharides with proteins. Additionally, the epimerases of the current invention may also be used modify industrially useful sugars which may be used as a stabilizer or gelling agent in some foods.

Variant and Mutant Polypeptides

To improve or alter the characteristics of a C5-epimerase polypeptide, protein engineering may be employed. Recombinant DNA technology known to those skilled in the art can be used to create novel mutant proteins or "muteins" including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions.

N-terminal and C-terminal Deletion Mutants

For instance, for many proteins, including the extracellular domain of a membrane associated protein or the mature form(s) of a secreted protein, it is known in the art that one or more amino acids may be deleted from the N-terminus or C-terminus without substantial loss of biological function. For instance, Ron et al., *J. Biol. Chem.*, 268:2984–2988 (1993), reported modified KGF proteins that had heparin binding activity even if 3, 8, or 27 amino-terminal amino acid residues were missing.

However, even if deletion of one or more amino acids from the N-terminus of a protein results in modification or loss of one or more biological functions of the protein, other biological activities may still be retained. Thus, the ability of the shortened protein to induce and/or bind to antibodies which recognize the complete or portion of the C5-epimerase protein generally will be retained when less than the majority of the residues of the complete protein or extracellular domain are removed from the N-terminus. Whether a particular polypeptide lacking N-terminal residues of a complete protein retains such immunologic activities can readily be determined by routine methods described herein and otherwise known in the art.

Accordingly, the present invention further provides polypeptides having one or more residues deleted from the amino terminus of the amino acid sequence shown in FIG. 3.

However, even if deletion of one or more amino acids from the C-terminus of a protein results in modification or loss of one or more biological functions of the protein, other biological activities may still be retained. Thus, the ability of the shortened protein to induce and/or bind to antibodies which recognize the complete or mature form of the protein generally will be retained when less than the majority of the residues of the complete or mature form protein are removed from the C-terminus. Whether a particular polypeptide lacking C-terminal residues of a complete protein retains such immunologic activities can readily be determined by routine methods described herein and otherwise known in the art.

The invention also provides polypeptides having one or more amino acids deleted from both the amino and the carboxyl termini.

Other Mutants

In addition to terminal deletion forms of the protein discussed above, it will also be recognized by one of ordinary skill in the art that some amino acid sequences of the C5-epimerase polypeptide can be varied without significant effect on the structure or function of the proteins. If such differences in sequence are contemplated, it should be remembered that there will be critical areas on the protein which determine activity. Thus, the invention further includes variations of the C5-epimerase polypeptide, which show substantial C5-epimerase polypeptide activity or which include regions of C5-epimerase protein such as the protein portions discussed below. Such mutants include deletions, insertions, inversions, repeats, and type substitutions. Guidance concerning which amino acid changes are likely to be phenotypically silent can be found in Bowie, J. U. et al., "Deciphering the Message in Protein Sequences: Tolerance to Amino Acid Substitutions," *Science* 247:1306–1310 (1990).

Thus, the fragment, derivative, or analog of the polypeptide of FIG. 3 or fusion protein containing the same, may be: (i) one in which one or more of the amino acid residues are substituted with a conserved or non-conserved amino acid residue (preferably a conserved amino acid residue(s), and more preferably at least one but less than ten conserved amino acid residue(s)), and such substituted amino acid residue(s) may or may not be one encoded by the genetic code; or (ii) one in which one or more of the amino acid residues includes a substituent group; or (iii) one in which the mature or soluble extracellular polypeptide is fused with another compound, such as a compound to increase the half-life of the polypeptide (for example, polyethylene glycol).; or (iv) one in which the additional amino acids are fused to a leader or secretory sequence or a sequence which is employed for purification of the mature polypeptide or a proprotein sequence. Such fragments, derivatives and analogs are deemed to be within the scope of those skilled in the art from the teachings herein.

Thus, the C5-epimerase of the present invention may include one or more amino acid substitutions, deletions or additions, either from natural mutations or human manipulation. As indicated, changes are preferably of a minor nature, such as conservative amino acid substitutions that do not significantly affect the folding or activity of the protein (see Table 1).

TABLE 1

Conservative Amino Acid Substitutions

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Amino acids in the C5-epimerase protein of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as receptor binding or in vitro proliferative activity.

Of particular interest are substitutions of charged amino acids with another charged amino acids and with neutral or negatively charged amino acids. The latter results in proteins with reduced positive charge to improve the characteristics of the C5-epimerase protein. The prevention of aggregation is highly desirable. Aggregation of proteins not only results in a loss of activity but can also be problematic when preparing pharmaceutical formulations, because they can be immunogenic. (Pinckard et al., *Clin Exp. Immunol.* 2:331–340 (1967); Robbins et al., *Diabetes* 36:838–845 (1987); Cleland et al. *Crit. Rev. Therapeutic Drug Carrier Systems* 10:307–377 (1993)).

The replacement of amino acids can also change the selectivity of binding of a ligand to cell surface receptors. For example, Ostade et al., *Nature* 361:266–268 (1993), describes certain mutations resulting in selective binding of TNF-α to only one of the two known types of TNF receptors. Sites that are critical for ligand-receptor binding can also be determined by structural analysis such as crystallization, nuclear magnetic resonance or photoaffinity labeling (Smith et al., *J. Mol. Biol.* 224:899–904 (1992) and de Vos et al., *Science* 255:306–312 (1992)).

The polypeptides of the present invention are preferably provided in an isolated form. By "isolated polypeptide" is intended a polypeptide removed from its native environment. The polypeptide produced and/or contained within a recombinant host cell is considered isolated for purposes of the present invention. Also intended as an "isolated polypeptide" are polypeptides that have been purified, partially or substantially, from a recombinant host cell. For example, a recombinantly produced version of the C5-epimerase polypeptide can be substantially purified by the one-step method described in Smith and Johnson, *Gene* 67:31–40 (1988). Preferably, the polypeptide of the invention is purified to a degree sufficient for sequence analysis, or such that it represents 99% of the proteinaceous material in the preparation.

The present inventors have discovered the mouse C5-epimerase gene and protein, and that the C5-epimerase polypeptide is a 618 residue protein exhibiting an N-terminal 154 amino acid domain, and especially a 33 or 34 amino acid domain containing amino acids 1–33 or 1–34 that is involved in secretion and stabilization of amino acid sequences that are linked to it. Accordingly, this domain, or a functional portion thereof, is useful for expression and secretion of proteins such as the C5-epimerase, or any other protein, especially a protein that associates with the Golgi apparatus or is otherwise associated with heparin or heparan sulfate synthesis.

The present inventors have also discovered that the N-terminus of the mouse C5-epimerase protein, and especially amino acids 1–154, 33–154 or 34–154, are especially useful to enhance the activity of other enzymes, especially other C5-epimerases. Accordingly, this domain, or a functional portion thereof, is useful for expression and secretion of fusion proteins that include C5-epimerase sequences heterologous to that shown in FIG. 3, especially the bovine C5-epimerase.

The polypeptides of the invention include the C5-epimerase polypeptide and fragments as discussed above, the amino acid sequence of which is at least 80% identical to a sequence selected from the group consisting of: (a) amino acids 1 to 118 of FIG. 3; (b) amino acids 1 to 119 of FIG. 3; (c) amino acids 1 to 120 of FIG. 3; (d) amino acids 1 to 121 of FIG. 3; (e) amino acids 119 to 618 of FIG. 3; (f) amino acids 120 to 618 of FIG. 3; (g) amino acids 121 to 618 of FIG. 3; (h) amino acids 122 to 618 of FIG. 3; (i) amino acids 34 to 147 of FIG. 3; (j) amino acids 35 to 154 of FIG. 3; (k) amino acids 34 to 154 of FIG. 3; (l) amino acids 1 to 154 of FIG. 3; and (m) the complete amino acid sequence as shown in FIG. 3.

The invention includes polypeptides which are at least 80% identical, more preferably at least 90% or 95% identical, still more preferably at least 96%, 97%, 98%, or 99% identical to the polypeptides described above, and also include portions of such polypeptides with at least 30 amino acids and more preferably at least 50 amino acids.

By a polypeptide having an amino acid sequence at least, for example, 95% "identical" to a reference amino acid sequence of a C5-epimerase polypeptide is intended that the amino acid sequence of the polypeptide is identical to the reference sequence except that the polypeptide sequence may include up to five amino acid alterations per each 100 amino acids of the reference amino acid of the C5-epimerase polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 90%, 95%, 96%, 97%, 98% or 99% identical to, for instance, the amino acid sequence shown in FIG. 3 can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The polypeptides of the present invention that possess C5-epimerase activity can be used to provide the same in vitro, for example, in developing assays for the same or in standardizing assays for use with more complex systems. The signal sequence of the invention can be used to secrete the homologous C5-epimerase enzyme from eukaryotic recombinant hosts, or to secrete heterologous sequences that are operably linked to the same. The activity enhancing sequence of the invention can be used to enhance the inherent epimerase activity of recombinant preparations of other C5-epimerases, and as such is best provided in the form of a gene encoding a fusion protein for the same.

Antibodies

C5-epimerase-protein specific antibodies for use in the present invention can be raised against the intact C5-epimerase proteins or an antigenic polypeptide fragment thereof, which may be presented together with a carrier protein, such as an albumin, to an animal system (such as rabbit or mouse) or, if it is long enough (at least about 25 amino acids), without a carrier, or in liposomes or complexed with PEG to enhance circulatory half-life.

As used herein, the term "antibody" (Ab) or "monoclonal antibody" (Mab) is meant to include intact molecules as well as antibody fragments (such as, for example, Fab and F(ab')$_2$ fragments) which are capable of specifically binding to a C5-epimerase protein. Fab and F(ab')$_2$ fragments lack the Fc fragment of intact antibody, clear more rapidly from the circulation, and may have less non-specific tissue binding of an intact antibody (Wahl et al., *J. Nucl. Med.* 24:316–325 (1983)). Thus, these fragments are preferred.

The antibodies of the present invention may be prepared by any of a variety of methods. For example, cells expressing the C5-epimerase protein or an antigenic fragment thereof can be administered to an animal in order to induce the production of sera containing polyclonal antibodies. In a preferred method, a preparation of C5-epimerase protein is prepared and purified to render it substantially free of natural contaminants. Such a preparation is then introduced into an animal in order to produce polyclonal antisera of greater specific activity.

In the most preferred method, the antibodies of the present invention are monoclonal antibodies. Such monoclonal antibodies can be prepared using hybridoma technology (Köhler et al., *Nature* 256:495 (1975); Köhler et al., *Eur. J. Immunol.* 6:511 (1976); Köhler et al., *Eur. J. Immunol.* 6:292 (1976); Hammerling et al., in: *Monoclonal Antibodies and T-Cell Hybridomas*, Elsevier, N.Y., (1981) pp. 563–681). In general, such procedures involve immunizing an animal (preferably a mouse) with a C5-epimerase protein antigen or, more preferably, with a C5-epimerase protein-expressing cell. Suitable cells can be recognized by their capacity to bind anti-C5-epimerase protein antibody. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100 μg/ml of streptomycin. The splenocytes of such mice are extracted and fused with a suitable myeloma cell line. Any suitable myeloma cell line may be employed in accordance with the present invention; however, it is preferable to employ the parent myeloma cell line (SP2O), available from the American Type Culture Collection, Manassas, Va. After fusion, the resulting hybridoma cells are selectively maintained in HAT medium, and then cloned by limiting dilution as described by Wands et al., *Gastroenterology* 80:225–232 (1981). The hybridoma cells obtained through such a selection are then assayed to identify clones which secrete antibodies capable of binding the desired C5-epimerase antigen.

Alternatively, additional antibodies capable of binding to the C5-epimerase antigen may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, C5-epimerase-protein specific antibodies are used to immunize an animal, preferably a mouse. The splenocytes of such an animal are then used to produce hybridoma cells, and the hybridoma cells are screened to identify clones which produce an antibody whose ability to bind to the C5-epimerase protein-specific antibody can be blocked by the C5-epimerase protein antigen. Such antibodies comprise anti-idiotypic antibodies to the C5-epimerase protein-specific antibody and can be used to immunize an animal to induce formation of further C5-epimerase protein-specific antibodies.

It will be appreciated that Fab and F(ab')$_2$ and other fragments of the antibodies of the present invention may be used according to the methods disclosed herein. Such fragments are typically produced by proteolytic cleavage, using enzymes such as papain (to produce Fab fragments) or pepsin (to produce F(ab')$_2$ fragments). Single chain antibodies, such as light or heavy chain antibodies, are also encompassed by this invention. Alternatively, C5-epimerase protein-binding fragments can be produced through the application of recombinant DNA technology or through synthetic chemistry. Such antibodies would include, but not be limited to recombinant abs which comprise complementarity determining regions (CDRs) that have differing binding specificities or CDRs which have been modified through the application of recombinant DNA technology or through synthetic chemistry to modify the binding specificity of the antibodies.

For in vivo use of anti-C5-epimerase in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. See, for review, Morrison, *Science* 229:1202 (1985); Oi et al., *Bio-Techniques* 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., *Nature* 312:643 (1984); Neuberger et al., *Nature* 314:268 (1985).

Bifunctional antibodies are antibodies which have antigen binding domains to different epitopes or derived from different species and are encompassed by the invention. Antibodies with Fc regions derived from species differing from the Fab regions are also envisioned and can be used in immunospecific chromatographic procedures. Also encompassed by this invention are antibodies with attached labels such as fluorescein, Texas Red, rhodamine, peroxidase, gold, magnetic labels, alkaline phosphatase, radioisotopes or chemiluminescent labels.

Having generally described the invention, the same will be more readily understood by reference to the following examples, which are provided by way of illustration and are not intended as limiting.

EXAMPLES

Example 1

Isolation and Sequencing of Mouse Genomic Clones

A mouse genomic library (FIX II, Stratagene) was screened with a DNA probe from a bovine sequence encoding C5-epimerase. The probe was labeled with $[\alpha^{32}P]dCTP$ (NEN Life Science Products). Approximately $2 \times 10^6$ phages were plated in a 20×20 cm plate and duplicate nylon filters were prepared from each plate. High stringency screening was performed with hybridization in 5× Denhardts, containing 100 µg of salmon sperm DNA/ml at 60° C. The final washes were in 0.1×SSC (1×SSC is 150 mM NaCl, 15 mM sodium citrate, pH 7.0 containing 0.1% SDS). Plaques that produced positive signals on both replicas were selected for second and third round screening, and ultimately five positive clones were isolated. It was found that two of the clones have a similar length of about 16 kb, while the other three were relatively shorter, around 10–12 kb. The longest clone (clone 64) was digested with Sac1 and the restriction fragments were cloned into pBlueScript. The second longest clone (clone 5A) was digested with EcoRI and resulting fragments were cloned into pUC119 for further characterization.

The insert containing plasmid was purified using the QIAGEN plasmid kit and sequenced. Nucleotide sequencing reaction was performed using the di-deoxy termination method, and was carried out with an ABI 310 sequencer. The exons and introns were determined by primer walking on both strands, and the size of the introns was estimated by sequencing in combination with agarose gel electrophoresis. There appear to be only 3 exons coding for the C5-epimerase, with the longest exon coding for more than 50% of the protein. The exon-intron junctions (splice sites) precisely follow the gt-ag consensus rule. Based on the presence of introns and the precise match between the exons and the cDNA sequence, we believe that the genomic clone identified represents the functional gene of the C5-epimerase.

Cloning of the Mouse C5-epimerase cDNA

One pair of primers was designed and based on the nucleotide sequence obtained by sequencing the exons of the genomic clone. The sense primer corresponds to bp 1–26 of the mouse ORF, starting from initiation codon ATG. The antisense primer corresponds to bp 1829–1854 without including the stop codon. PCR was performed by using a mouse liver QUICK-Clone™ cDNA (Clontech) as template at the conditions: 1 cycle of 94° C. for 1 min, 30 cycles each of 94° C. for 30 s, 60° C. for 45 s and 72° C. for 1 min, and a final extension at 72° C. for 10 min. A strong band of about 2 kb was obtained, which was cloned into a TOPO™-TA Cloning vector (Invitrogen) and amplified and subsequently sequenced. By double strand sequencing it was found the mouse C5-epimerase clone is 1875 bp long, with a strong hydrophobic domain at N-terminal of the deduced peptide.

Northern Blot Analysis

The mouse multi-tissue mRNA blot was purchased from Clontech. The DNA probe from bovine cDNA clone was labeled with $[\alpha^{32}P]dCTP$ by Klenow enzyme from Boehringer Mannheim. The hybridization was carried out in ExpressHyb (Clontech) at 60° C. for one hour and washed at high stringency. The membrane was exposed to Kodak film at −70° C. overnight. The C5-epimerase enzyme is expressed in all tissues examined and the transcript is around 5 kb. It seems that the liver has the highest expression for the transcript, while the spleen expresses a relatively lower level relative to β-actin in the same membrane.

Southern Blot Analysis

Southern blot analysis was performed according to Sambrook et al. (Sambrook et al., 1989). Mouse genomic DNA was prepared with an Easy Prep kit (Pharmacia Biotech). 20 µg of genomic DNA was digested with restriction enzyme SacI, and separated on a 0.8% agarose gel by electrophoresis. After electrophoresis, the gel was treated with 0.1N NaOH for 30 min and neutralized in Tris-HCl buffer. The DNA fragments were transferred onto a nylon membrane. A 837 bp fragment of bovine C5-epimerase cDNA was labeled with $[\alpha^{32}P]dCTP$ by Klenow enzyme from Boehringer Mannheim and used as probe. The hybridization conditions were carried out as described for Northern analysis. The exposure time was 3 days.

To determine how many genes may potentially code for C5-epimerase, twenty micrograms of mouse genomic DNA purified from mouse liver was digested with restriction enzymes of ApaI, BamHI, EcoRI, EcoRV, HindIII, NcoI and XbaI respectively and separated on a 0.8% agarose gel by electrophoresis. The DNA separated in the gel was transferred to a Nylon membrane and was subsequently hybridized with a DNA probe from bovine coding sequence (1407 bp). The restriction map of the C5-epimerase genomic DNA suggests that there is only one gene coding for the C5-epimerase enzyme in mice.

Enzyme Activity Analysis

The activity of C5-epimerase was assessed according to the protocol as disclosed in Malmstrom et al., *J. Biol. Chem.* 255:3878–3883 (1980), which is herein incorporated by reference. Briefly, a mouse, transplanted with mastocytoma cells intramuscularly, was euthanized by cervical dislocation and then dissected. The respective tissues, including the xenograft, were taken and were immediately homogenized in a buffer of 50 mM HEPES containing 100 mM KCl, 15 mM EDTA, 1% Triton X-100 and protease inhibitors. The homogenates were shaken at 4° C. for 30 min and centrifuged. The supernatant was collected. Total protein concentration was determined by QuantiGold assay, and the specific activity of C5-epimerase was analyzed based on the release of $^3H$ (recovered as $^3H_2O$) from a substrate polysaccharide according to the procedure described by Li et al. (Li et al. 1997). The C5-substrate used in the specific activity test is analyzed at least once a month by measuring only 50 µl C5-substrate working solution without any enzyme.

If the initial activity of the sample is >2000 cpm/50 µl, this is an indication that the sample is saturated and needs to be diluted. Dilution factors depend on the samples used, the saturation of the samples and on the salt concentration. The sample must contain not more than 50 mM salt (NaCl or KCl), because the C5-epimerase activity is partially or completely inhibited at higher salt concentrations.

Positive and negative controls are used in C5-epimerase activity assay. The positive control has to be standardized every two months to be sure that the stability has been preserved. Only a vector produced in the same cells as the sample can be used as a negative control. For example, for the C5-samples produced by baculovirus/insect cell expression system acetylcholinesterase produced with the same system has been used as a negative control.

During the prewarming of the C5 substrate solution, the samples were diluted if needed. 50 µl sample (enzyme) was added to the prewarmed substrate and incubated exactly for 1 h at +37° C. After incubation 100 μl of a stop solution of enzyme reaction was added to the substrate-enzyme mixture, and this reaction mixture was transferred to a Wallac's 20 ml scintillation vial. 13 ml of epimerase assay scintillation cocktail was added to the vials and vortexed for 10 s. Radioactivity was measured in triplicate with a Wallac 1415 Liquid Scintillation Counter for 2 minutes each, after overnight incubation. The scintillation counter gives the results as cpm/reaction volume (50 μl). If a sample has been diluted, the activity of the dilution buffer should be subtracted from sample's activity. In any case, the activity of the blank was subtracted from the activity of the sample before analyzing the results.

Specific activity was measured by dividing total activity (cpm/μl) by total protein concentration (mg/ml). Total protein concentration was measured by QuantiGold assay according to Stoschek, C. M., *Anal. Biochem.* 160:301–305 (1987), which is herein incorporated by reference. The unit of specific activity is cpm/mg/h, where h (hour) describes the time of the enzyme reaction.

Example 2

Identification of the True N-terminus of C5-epimerase From Coding Sequence Analysis of Mouse Gene, and Expression of Cloned cDNA Based on cloning and preliminary sequence analysis of the putative mouse C5-epimerase gene identified in Example 1, and based on alignment to the previously published bovine cDNA sequence, additional murine 5'-flanking DNA sequence was isolated, and a cDNA was cloned that contained this 5'-flanking DNA sequence.

To determine if this 5'-flanking DNA sequence might encode additional N-terminal peptide sequences that would represent the true N-terminus of the C5-epimerase encoded by the mouse gene, the mouse sequence (bold text in the compiled nucleotide sequence shown in FIG. 1) was added to the bovine cDNA sequence, which was already in a computer file, using the bovine sequence and starting from point of greatest conservation (>96% amino acid identity). Then, the Gene Inspector program (Textco, USA) was used to search for open reading frames (ORFs) which are potential polypeptide coding sequences) in the compiled sequence. The result of the sequence alignment is shown in FIG. 1 and the ORF analysis yielded the results shown in FIG. 2.

In FIG. 1, the fusion site between the new mouse sequence and the bovine sequence is indicated by the double colon "::". The sequence beginning following the double colon is the bovine cDNA sequence. The sequence (in bold) 5' to the fusion site is the additional murine 5'-flanking DNA sequence isolated as described above. The underlined sequence is the open reading frame that was found, showing the polypeptide coding sequence.

It is known that the native C5-epimerase enzyme is localized to the membranous golgi "compartment" (microsomal fraction) of cells (from liver). Therefore, the native mouse sequence should contain a suitable N-terminal signal for translocation to this compartment. To analyze this, the algorithm (program) of Nielsen et al., *Protein Engineering* 10:1–6 (1997), was used. The algorithm analyzed the "signal" potential of the first 40–60 amino acids from each of the above polypeptide sequences. The same program was used to test the first 40 residues of the mouse syndecan-1 polypeptide sequence, as this is known to contain a secretion signal, as a sort of control for efficacy of the program, and the program positively identified this (data not shown). The analysis demonstrated strong signal potential for the first 33 residues.

Besides the 33 amino acid signal sequence already mentioned, the 154 additional N-terminal residues include additional cysteine residues which might form disulfide bonds and stabilize protein folding, and a predicted amidation site (residues 118–121) that might be relevant to post-translational proteolytic processing. Further analyses of the complete sequence for C5-epimerase predicts hydrophobic stretches of polypeptide which could be buried, or traverse membrane(s).

Alignment analysis to other sequences found in databases reveal hotspots of homology. These results are summarized in FIGS. 4 and 5.

FIG. 5 is a diagrammatic representation of the mouse C5-epimerase polypeptide sequence. As shown on FIG. 5, the greatest evolutionary conservation ("hotspots" of homology) of sequence has occurred in the more C-terminal portion, in a highly hydrophobic stretch between amino acid residues Trp497 and Leu523, predicted to be buried in the protein's folded structure or traversing a membrane, possibly into the lumen of the golgi, where the enzyme is known to act. The other most significant and extended stretch ("hotspot") of conservation occurs between residues Leu546 and His580, and might contain or comprise the active site of the enzyme. The functional significance of polypeptide sequence conservation (identity) ≧22% has been established by published studies of other proteins of known function (Branden, C., and Tooze, J., *Introduction to Protein Structure*, Garland Publishing, NY and London, pp. 100–101 (1991))., and Wilson, Kreychman, and Gerstein and the other authors cited therein, in "Quantifying the relations between protein sequence, structure, and function through traditional and probabilistic scores," available at bioinfo.mbb.yale.edu/e-print/ann-xfer-jmb/preprint. As explained in this article, precise function does not appear to be conserved below 30–40% sequence identity, whereas functional class is conserved for sequence identities as low as 20–25%. Below 20%, general similarity is no longer conserved.). At present, SWISS-MODEL will generate models for sequences which respond to these criteria: BLAST search P value: <0.00001; Global degree of sequence identity (SIM): >25% and Minimal projected model length—25 amino acids.

Based on this, it is seen that the *Drosophila* sequence is more closely related (46.6%) than the *C. elegans* sequence (39.6%) to the mouse sequence.

In another type of sequence analysis, the predicted three-dimensional (3D) structure of the mouse C5-epimerase sequence was "threaded" against the 3D structures of Kelley, L. A., et al., *Mol. Biol.* 299(2):499–520 (2000). This comparison indicated that the C5-epimerase sequence has a significant relationship to a chondroitinase (chondroitin AC/alginate lyase) domain, which is an alpha/alpha toroid. The chondroitin AC lyase is representative of a family of glycosaminoglycan degrading enzymes, and structure/function relationships have been elucidated from crystallography (Fethiere et al., *J. Mol. Biol.* 288:635–647 (1999). Remarkably, the most significant 3D similarity to the chondroitinase sequence was found to extend from Ala408, near the C-terminal end of an internal hydrophobic (transmembrane) stretch, to the C-terminus of the mouse C5-epimerase sequence, and that this stretch contains most of the conserved sequence conservation likely indicates that it is a domain containing the active site.

Based on all the above sequence analyses results, new recombinant C5-epimerase constructs were made, in addition to the first active tagged recombinant (bovine) C5-epimerase construct, for heterologous secretion-expression from baculovirus and InsectSelect (Invitrogen, USA) expression systems. The products from cloned insect cell lines so far characterized are summarized in FIG. 6A. Four constructs are shown. The first construct is the tagged recombinant bovine C5-epimerase. The second construct is the tagged full length mouse C5-epimerase. The third construct is a tagged, chimeric construct between the mouse and bovine C5-epimerase sequences. The fourth construct is a tagged, truncated mouse sequence.

In each of the recombinant constructs, the C5-epimerase was tagged. When tagged, the C5-epimerase sequence was preceded by a sequence as shown in FIG. 6B which contains the EGT signal peptide linked to the EGT signal cleavage, an enterokinase cleavage site, six histidines, and finally the rTEV protease site. The EGT signal is from a protein of baculovirus (which infects insect cells). The FLAG sequence is an epitope-tag used for detecting and purifying recombinant protein according to the manufacturer's suggested protocol (Sigma) (Hopp, T. et al., *Biotechnology* 6:1204–1210 (1988)). Enterokinase is an enzyme used to cleave off the sequence preceding its recognition site. The six consecutive histidines are another tag. The rTEV (recombinant tobacco edge virus) protease-site was also used to remove the preceding sequences. The EGT signal and FLAG™-tag (IBI) were obtained from constructs made in a modified pFastBac™ (Life Technologies) vector provided by Dr. Christian Over-Blom, VTT Biotechnology, P.O. Box 1500, FIN-02044, VTT, FINLAND. The purification of all recombinant proteins described in this application was FLAG-tag-based.

Figure 7:
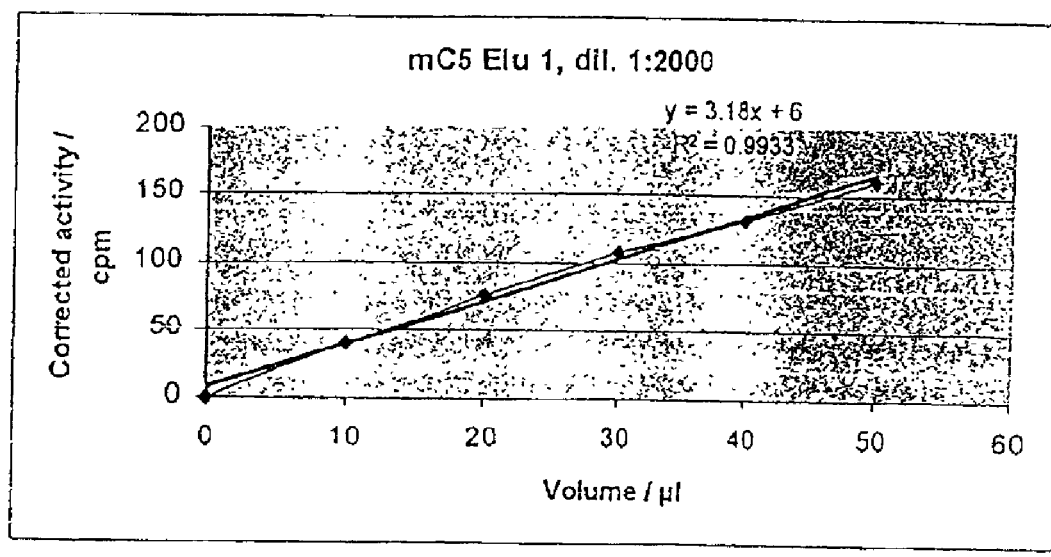
FIG. 7. Activity assay results of mouse C5-epimerase (mC5).

The representative data from activity assays and protein analyses of these tagged recombinant C5-epimerases are shown in FIG. 7, and Table I and Table II. FIG. 7 shows activity assay results of mouse C5-epimerase (mC5) that had been purified over anti-FLAG M1 according to the manufacturer's suggested protocol.

The C5-epimerase activity assay to measure the activity of the heterologous protein was performed as in Example 1 above. Briefly, total protein was extracted from cultures transformed with each of the recombinant C5-epimerase constructs that were individually inoculated into insect cells using the InsectSelect expression systems. After the cells reached confluence, they were harvested and lysed and total protein was isolated and quantitated. C5-epimerase activity was measured as $^3$H release from the epimerase substrate in a scintillation counter. Epimerase activity was measured against total protein. FIG. 7 shows the activity with increasing volume of sample (diluted 1:2000). The total activity was 6360 cpm/µl. Protein analysis (using QuantiGold, Diversified Biotech) was analyzed according to Stoschek, C. M., *Anal. Biochem.* 160:301–305 (1987) and indicated that the concentration of protein was 3.2 µg/ml. Therefore, the specific activity was $2.0 \times 10^9$ cpm/mg/h.

Figure 8:
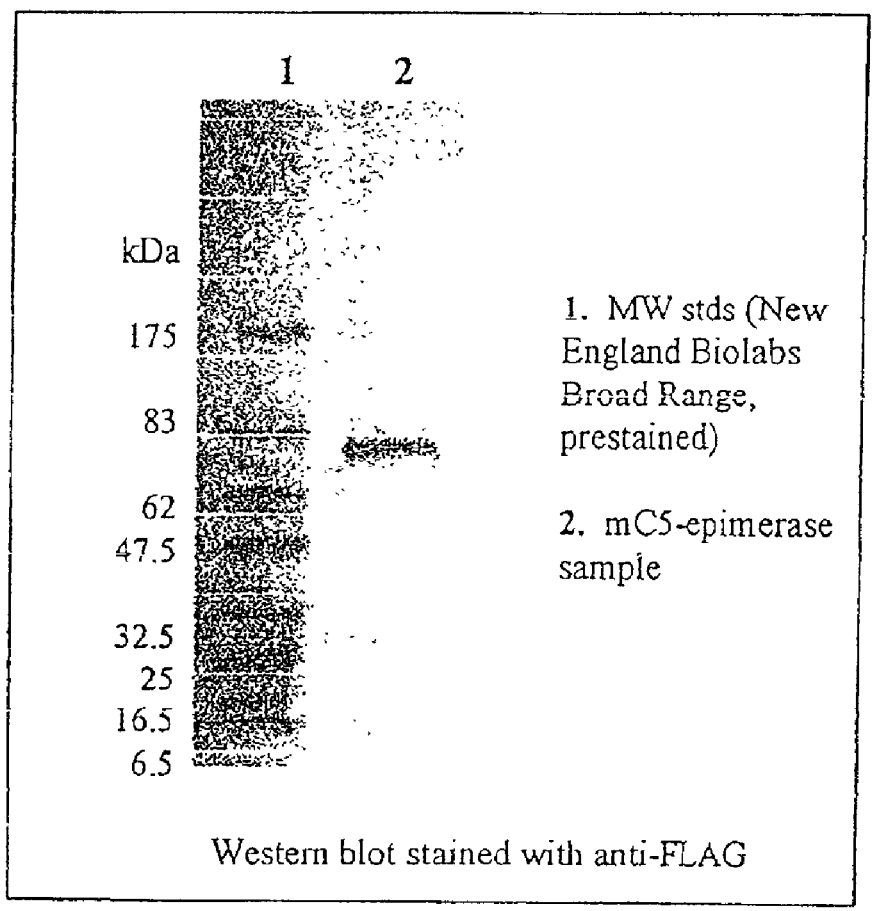
FIG. 8. Western blot stained with anti-FLAG. Lane 1: molecular weight standards (New England Biolabs' Broad Range, prestained). Lane 2: mouse C5-epimerase (mC5) sample.

FIG. 8 shows a Western blot stained with anti-FLAG. Lane 1 contains molecular weight standards (New England Biolabs, Broad Range, prestained). Line 2 contains the full-length mouse C5-epimerase. The tagged full-length mouse C5-epimerase (that contains the N-terminal additional sequences found herein) has a length of 618 amino acids, a molecular weight (daltons) of 71189.1, an isoelectric point (pI) of 8.25 and a net charge at pH 7 of +4.01.

Figure 9:
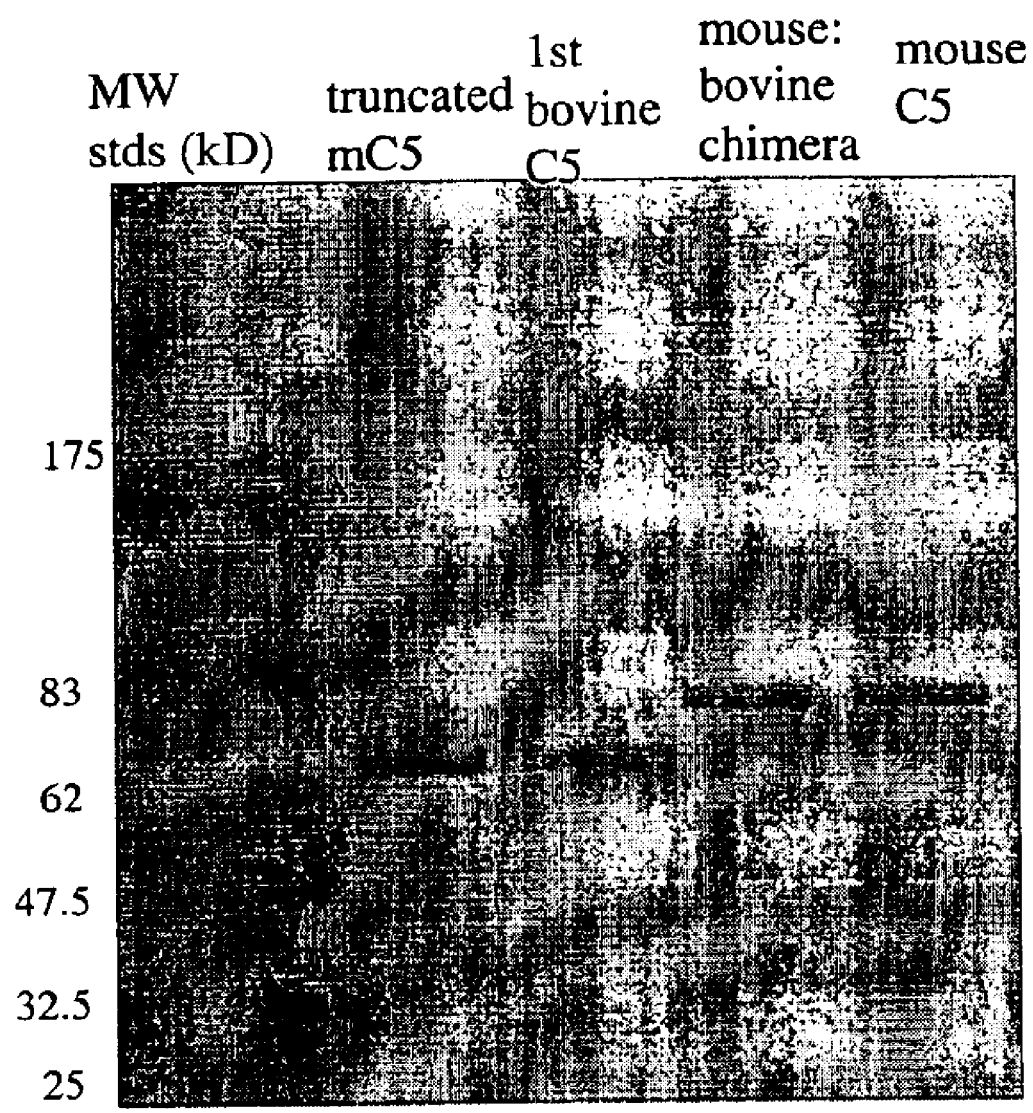
FIG. 9. Western blot of the proteins in the medium from stable insect cell lines of clones containing different tagged recombinant C5-epimerases stained with anti-FLAG antibody.

FIG. 9 is a Western blot of the culture medium taken from stable insect cell lines of the different clones for the four tagged recombinant C5-epimerases described above, stained with anti-FLAG antibody (020300). Lane 1 contains molecular weight standards as in FIG. 8, with the molecular weights noted on the side of the gel. Lane 2 contains the truncated mouse C5-epimerase. Lane 3 contains the original bovine C5-epimerase. Lane 4 contains the mouse:bovine chimeric C5-epimerase in which the N-terminal mouse sequences are fused in frame to the bovine sequences, as shown in FIGS. 2 and 3. Lane 5 contains the full-length mouse C5-epimerase. It can be seen that the chimeric mouse: bovine construct is approximately the same size as that of the full-length mouse construct.

The relative activity of the different recombinant constructs was calculated based on the activity assays and densitometric analysis of the Western Blot and is shown in Table I, below. "TruncC5" is the shortened mouse C5-epimerase amino acid sequence where the first 154 amino acids have been removed such that the "TruncC5" sequence has the same N-terminus as the recombinant bovine sequence. "ExtC5" is the recombinant bovine C5-epimerase polypeptide, while "chC5" refers to the mouse:bovine chimeric C5-epimerase construct encoded by the nucleic acid sequence as shown in FIG. 1. "mC5" refers to the full-length mouse C5-epimerase sequence.

TABLE I

Relative activities of different recombinant C5-epimerases.

| Sample | Density | Sample (µl) | Density/µl | Activity (cpm/µl) | Activity/Density (Cpm/densitometric unit) |
|---|---|---|---|---|---|
| truncC5 | 15984 | 12 | 1332.0 | 20 | 0.015 |
| extC5 | 6451 | 12 | 537.6 | 7 | 0.013 |
| chC5 | 14960 | 12 | 1246.7 | 3455 | 2.771 |
| mC5 | 13804 | 12 | 1150.3 | 3681 | 3.200 |

The Specific activities of the different partially-purified recombinant C5-epimerases is shown in Table II.

TABLE II

Specific activities of the Partially-purified recombinant C5-epimerases.

| Sample | Total activity (cpm/µl) | Linearity ($R^2$) | Protein (mg/ml) | Specific Activity (cpm/mg/h) |
|---|---|---|---|---|
| truncC5 | 39.5 | 0.9905 | 0.0129 | $3.06 \times 10^6$ |
| extC5 | 9.1 | 0.9978 | 0.0092 | $9.89 \times 10^5$ |
| chC5 | 919.7 | 0.9964 | 0.0026 | $3.54 \times 10^8$ |
| mC5 | 2019 | 0.9969 | 0.0042 | $4.81 \times 10^8$ |

The chimeric mouse:bovine construct that was made contains amino acid residues 34–154 of the N-terminal sequence of the mouse polypeptide sequence, immediately following the EGT-FLAG-His-RTEV elements as shown in FIG. 6B. However, that recombinant enzyme appeared to be predominantly retained in the cytosol, probably due to the signaling potential of the mouse sequence.

Conclusion

The addition of an N-terminal fragment of polypeptide (Asp34 to Asp154) from the mouse gene sequence enhances the activity of recombinant C5-epimerase enzyme by orders of magnitude, even though this piece of sequence does not contain the greatest interspecies conservation. The possible effect of tags on activity of the first recombinant bovine construct has been addressed (by tag removal; data not shown), and might account for a minor factor of the difference, but not to the extent of the orders of magnitude differences in specific activities between longer and shorter forms of recombinant C5-epimerase. Untagged expression constructs and structure-function studies are currently underway to better define the basis and mechanism for controlling the activity of this very important recombinant enzyme.

What is claimed is:

1. An isolated polynucleotide comprising a nucleotide sequence encoding a polypeptide, the amino acid sequence of which is at least 95% identical to amino acids 1–618 of FIG. 3. (SEQ ID No. 2), wherein said amino acid sequence encodes a polypeptide that has C5-epimerase enzymatic activity.

2. The polynucleotide of claim 1 which is DNA.

3. The polynucleotide of claim 1 which is RNA.

4. The polynucleotide of claim 1, further comprising a heterologous polynucleotide.

5. The polynucleotide of claim 4, wherein said heterologous polynucleotide encodes a heterologous polypeptide.

6. The polynucleotide of claim 5, wherein said heterologous polynucleotide is positioned at the 3' of said nucleotide sequence.

7. A vector comprising the polynucleotide of any one of claims 1–6.

8. The vector of claim 7, wherein said polynucleotide is operably linked to a heterologous regulatory polynucleotide.

9. A host cell comprising the polynucleotide of any one of claims 1–6.

10. The host cell of claim 9, wherein said isolated polynucleotide is operably linked to a heterologous regulatory polynucleotide.

11. A method of producing a protein that comprises culturing the host cell of claim 10 under conditions such that said protein is expressed, and recovering said protein.

12. A method of increasing the activity of a C5-epimerase, said method comprising:

(a) providing a first polynucleotide comprising a nucleotide sequence encoding a polypeptide, the amino acid sequence of which is at least 80% identical to a reference amino acid sequence selected from the group consisting of amino acids 35 to 154 of FIG. 3 and amino acids 34 to 154 of FIG. 3;

(b) attaching said first polynucleotide of (a) in frame to the N-terminus of a second polynucleotide encoding a C5-epimerase; and (c) expressing the fusion polynucleotide, wherein the C5-epimerase that is encoded by said fusion polynucleotide has an increased C5-epimerase activity when compared to the C5-epimerase activity of said polypeptide that is encoded by said second polynucleotide.

13. The method of claim 12, wherein said first polynucleotide comprises a nucleotide sequence encoding a polypeptide, the amino acid sequence of which is amino acids 35 to 154 of FIG. 3.

14. The method of claim 12, wherein said first polynucleotide comprises a nucleotide sequence encoding a polypeptide, the amino acid sequence of which is amino acids 34 to 154 of FIG. 3.

15. The method of any one of claims 12–14, wherein said second polynucleotide encoding a C5-epimerase encodes bovine C5-epimerase.

* * * * *

SEQUENCE LISTING

<160> NUMBER OF SEQ ID NOS: 11

<210> SEQ ID NO 1
<211> LENGTH: 1854
<212> TYPE: DNA
<213> ORGANISM: Mus musculus
<220> FEATURE:
<221> NAME/KEY: CDS
<222> LOCATION: (1)..(1854)

<400> SEQUENCE: 1

```
atg cgt tgt ttg gca gct cgg gtc aac tat aag act ttg att atc atc      48
Met Arg Cys Leu Ala Ala Arg Val Asn Tyr Lys Thr Leu Ile Ile Ile
1               5                   10                  15 tgt gcg cta ttc act ttg gtc aca gta ctt ttg tgg aat aag tgt tcc      96
Cys Ala Leu Phe Thr Leu Val Thr Val Leu Leu Trp Asn Lys Cys Ser
                20                  25                  30 agc gac aaa gca atc cag ttt cct cgg cac ttg agt agt gga ttc aga     144
Ser Asp Lys Ala Ile Gln Phe Pro Arg His Leu Ser Ser Gly Phe Arg
            35                  40                  45 gtg gat gga tta gaa aaa aga tca gca gca tct gaa agt aac cac tat     192
Val Asp Gly Leu Glu Lys Arg Ser Ala Ala Ser Glu Ser Asn His Tyr
        50                  55                  60 gcc aac cac ata gcc aaa cag cag tca gaa gag gca ttt cct cag gaa     240
Ala Asn His Ile Ala Lys Gln Gln Ser Glu Glu Ala Phe Pro Gln Glu
65                  70                  75                  80 caa cag aag gca ccc cct gtt gtt ggg ggc ttc aat agc aac ggg gga     288
Gln Gln Lys Ala Pro Pro Val Val Gly Gly Phe Asn Ser Asn Gly Gly
                85                  90                  95 agc aag gtg tta ggg ctc aaa tat gaa gag att gac tgt ctc ata aac     336
Ser Lys Val Leu Gly Leu Lys Tyr Glu Glu Ile Asp Cys Leu Ile Asn
                100                 105                 110 gat gag cac acc att aaa ggg aga cga gag ggg aat gaa gtt ttc ctt     384
Asp Glu His Thr Ile Lys Gly Arg Arg Glu Gly Asn Glu Val Phe Leu
            115                 120                 125 cca ttc act tgg gta gag aaa tac ttt gat gtt tat gga aaa gtg gtc     432
Pro Phe Thr Trp Val Glu Lys Tyr Phe Asp Val Tyr Gly Lys Val Val
        130                 135                 140 cag tat gac ggc tat gat cga ttt gaa ttc tct cat agc tat tcc aaa     480
Gln Tyr Asp Gly Tyr Asp Arg Phe Glu Phe Ser His Ser Tyr Ser Lys
145                 150                 155                 160 gtc tat gca cag aga tca cct tat cac cct gac ggt gtg ttt atg tcc     528
Val Tyr Ala Gln Arg Ser Pro Tyr His Pro Asp Gly Val Phe Met Ser
                165                 170                 175 ttt gaa ggc tac aat gtg gaa gtc cga gac aga gtc aaa tgt ata agt     576
Phe Glu Gly Tyr Asn Val Glu Val Arg Asp Arg Val Lys Cys Ile Ser
                180                 185                 190 gga gtt gaa ggt gtg cca tta tct acc cag tgg ggg cct caa ggc tat     624
Gly Val Glu Gly Val Pro Leu Ser Thr Gln Trp Gly Pro Gln Gly Tyr
            195                 200                 205 ttc tac cca atc cag att gca cag tat ggg cta agt cat tac agc aag     672
Phe Tyr Pro Ile Gln Ile Ala Gln Tyr Gly Leu Ser His Tyr Ser Lys
        210                 215                 220 aat cta acc gag aaa ccc cct cac ata gaa gta tat gaa aca gca gaa     720
Asn Leu Thr Glu Lys Pro Pro His Ile Glu Val Tyr Glu Thr Ala Glu
```

```
                                                    -continued
       225                 230                 235                 240
gac agg gac aga aac atc aga cct aat gaa tgg act gtg ccc aag ggg         768
Asp Arg Asp Arg Asn Ile Arg Pro Asn Glu Trp Thr Val Pro Lys Gly
                    245                 250                 255 tgc ttc atg gcc agt gtg gca gac aag tct aga tcc acc aat gtt aaa         816
Cys Phe Met Ala Ser Val Ala Asp Lys Ser Arg Ser Thr Asn Val Lys
                260                 265                 270 cag ttt att gct cca gaa acc agt gaa ggt gtg tct ttg cag ctg gga         864
Gln Phe Ile Ala Pro Glu Thr Ser Glu Gly Val Ser Leu Gln Leu Gly
            275                 280                 285 aac aca aaa gac ttc att att tca ttt gac ctc aag ctt tta aca aat         912
Asn Thr Lys Asp Phe Ile Ile Ser Phe Asp Leu Lys Leu Leu Thr Asn
        290                 295                 300 ggg agt gtg tct gtg gtt ctg gag acc aca gaa aag aat cag ctc ttc         960
Gly Ser Val Ser Val Val Leu Glu Thr Thr Glu Lys Asn Gln Leu Phe
    305                 310                 315                 320 act gtg cat tat gtc tca aac acc cag ctg att gct ttc aga gac agg        1008
Thr Val His Tyr Val Ser Asn Thr Gln Leu Ile Ala Phe Arg Asp Arg
                    325                 330                 335 gac ata tac tac ggc att ggg ccc aga act tca tgg agt aca gtt acc        1056
Asp Ile Tyr Tyr Gly Ile Gly Pro Arg Thr Ser Trp Ser Thr Val Thr
                340                 345                 350 aga gac ctg gtc act gac ctc agg aaa gga gtg ggc ctt tct aac aca        1104
Arg Asp Leu Val Thr Asp Leu Arg Lys Gly Val Gly Leu Ser Asn Thr
            355                 360                 365 aaa gct gtc aag cca acc aaa atc atg ccc aaa aag gtg gtt agg ttg        1152
Lys Ala Val Lys Pro Thr Lys Ile Met Pro Lys Lys Val Val Arg Leu
        370                 375                 380 att gca aaa ggg aag gga ttc ctg gac aac att acc atc tca acc aca        1200
Ile Ala Lys Gly Lys Gly Phe Leu Asp Asn Ile Thr Ile Ser Thr Thr
    385                 390                 395                 400 gcc cac atg gct gca ttc ttt gct gca agt gac tgg cta gtg agg aac        1248
Ala His Met Ala Ala Phe Phe Ala Ala Ser Asp Trp Leu Val Arg Asn
                    405                 410                 415 cag gat gag aaa ggt ggc tgg cca att atg gtg acc cgg aag tta ggg        1296
Gln Asp Glu Lys Gly Gly Trp Pro Ile Met Val Thr Arg Lys Leu Gly
                420                 425                 430 gaa ggg ttt aaa tct tta gaa cca gga tgg tac tct gcc atg gca caa        1344
Glu Gly Phe Lys Ser Leu Glu Pro Gly Trp Tyr Ser Ala Met Ala Gln
            435                 440                 445 ggg caa gcc atc tct acc tta gtc agg gcc tat ctt cta acg aaa gac        1392
Gly Gln Ala Ile Ser Thr Leu Val Arg Ala Tyr Leu Leu Thr Lys Asp
        450                 455                 460 tat gta ttc ctc agt tca gct tta agg gca aca gcc cca tac aag ttt        1440
Tyr Val Phe Leu Ser Ser Ala Leu Arg Ala Thr Ala Pro Tyr Lys Phe
    465                 470                 475                 480 ccg tca gag cag cat gga gtt aaa gcc gtg ttc atg aat aaa cat gac        1488
Pro Ser Glu Gln His Gly Val Lys Ala Val Phe Met Asn Lys His Asp
                    485                 490                 495 tgg tat gaa gaa tat cca acc aca cct agc tct ttt gtt tta aat ggc        1536
Trp Tyr Glu Glu Tyr Pro Thr Thr Pro Ser Ser Phe Val Leu Asn Gly
                500                 505                 510 ttt atg tat tct tta att ggg ctg tat gac cta aaa gaa aca gca ggg        1584
Phe Met Tyr Ser Leu Ile Gly Leu Tyr Asp Leu Lys Glu Thr Ala Gly
            515                 520                 525 gag aca ctt ggg aaa gaa gca agg tcc ttg tac gag cgc ggc atg gaa        1632
Glu Thr Leu Gly Lys Glu Ala Arg Ser Leu Tyr Glu Arg Gly Met Glu
        530                 535                 540 tct ctt aaa gcc atg ctg ccc ttg tat gat act ggc tcc ggg acc atc        1680
```

-continued

```
Ser Leu Lys Ala Met Leu Pro Leu Tyr Asp Thr Gly Ser Gly Thr Ile
545                 550                 555                 560 tat gac ctc cgc cac ttc atg ctt ggc att gct ccc aac ctg gcc cgc    1728
Tyr Asp Leu Arg His Phe Met Leu Gly Ile Ala Pro Asn Leu Ala Arg
                    565                 570                 575 tgg gac tat cac acc acc cac att aac cag ctg cag ctg ctc agc acc    1776
Trp Asp Tyr His Thr Thr His Ile Asn Gln Leu Gln Leu Leu Ser Thr
                580                 585                 590 atc gat gag tcc cca atc ttc aaa gaa ttt gtc aag agg tgg aaa agc    1824
Ile Asp Glu Ser Pro Ile Phe Lys Glu Phe Val Lys Arg Trp Lys Ser
            595                 600                 605 tac ctt aaa ggc agt agg gca aag cac aac                            1854
Tyr Leu Lys Gly Ser Arg Ala Lys His Asn
        610                 615

<210> SEQ ID NO 2
<211> LENGTH: 618
<212> TYPE: PRT
<213> ORGANISM: Mus musculus

<400> SEQUENCE: 2

Met Arg Cys Leu Ala Ala Arg Val Asn Tyr Lys Thr Leu Ile Ile Ile
1               5                   10                  15

Cys Ala Leu Phe Thr Leu Val Thr Val Leu Leu Trp Asn Lys Cys Ser
            20                  25                  30

Ser Asp Lys Ala Ile Gln Phe Pro Arg His Leu Ser Ser Gly Phe Arg
        35                  40                  45

Val Asp Gly Leu Glu Lys Arg Ser Ala Ala Ser Glu Ser Asn His Tyr
    50                  55                  60

Ala Asn His Ile Ala Lys Gln Gln Ser Glu Glu Ala Phe Pro Gln Glu
65                  70                  75                  80

Gln Gln Lys Ala Pro Pro Val Val Gly Gly Phe Asn Ser Asn Gly Gly
                85                  90                  95

Ser Lys Val Leu Gly Leu Lys Tyr Glu Glu Ile Asp Cys Leu Ile Asn
            100                 105                 110

Asp Glu His Thr Ile Lys Gly Arg Arg Glu Gly Asn Glu Val Phe Leu
        115                 120                 125

Pro Phe Thr Trp Val Glu Lys Tyr Phe Asp Val Tyr Gly Lys Val Val
    130                 135                 140

Gln Tyr Asp Gly Tyr Asp Arg Phe Glu Phe Ser His Ser Tyr Ser Lys
145                 150                 155                 160

Val Tyr Ala Gln Arg Ser Pro Tyr His Pro Asp Gly Val Phe Met Ser
                165                 170                 175

Phe Glu Gly Tyr Asn Val Glu Val Arg Asp Arg Val Lys Cys Ile Ser
            180                 185                 190

Gly Val Glu Gly Val Pro Leu Ser Thr Gln Trp Gly Pro Gln Gly Tyr
        195                 200                 205

Phe Tyr Pro Ile Gln Ile Ala Gln Tyr Gly Leu Ser His Tyr Ser Lys
    210                 215                 220

Asn Leu Thr Glu Lys Pro Pro His Ile Glu Val Tyr Glu Thr Ala Glu
225                 230                 235                 240

Asp Arg Asp Arg Asn Ile Arg Pro Asn Glu Trp Thr Val Pro Lys Gly
                245                 250                 255

Cys Phe Met Ala Ser Val Ala Asp Lys Ser Arg Ser Thr Asn Val Lys
            260                 265                 270

Gln Phe Ile Ala Pro Glu Thr Ser Glu Gly Val Ser Leu Gln Leu Gly
```

```
                275                 280                 285
Asn Thr Lys Asp Phe Ile Ile Ser Phe Asp Leu Lys Leu Leu Thr Asn
290                 295                 300

Gly Ser Val Ser Val Val Leu Glu Thr Thr Glu Lys Asn Gln Leu Phe
305                 310                 315                 320

Thr Val His Tyr Val Ser Asn Thr Gln Leu Ile Ala Phe Arg Asp Arg
                325                 330                 335

Asp Ile Tyr Tyr Gly Ile Gly Pro Arg Thr Ser Trp Ser Thr Val Thr
                340                 345                 350

Arg Asp Leu Val Thr Asp Leu Arg Lys Gly Val Gly Leu Ser Asn Thr
                355                 360                 365

Lys Ala Val Lys Pro Thr Lys Ile Met Pro Lys Lys Val Val Arg Leu
370                 375                 380

Ile Ala Lys Gly Lys Gly Phe Leu Asp Asn Ile Thr Ile Ser Thr Thr
385                 390                 395                 400

Ala His Met Ala Ala Phe Phe Ala Ala Ser Asp Trp Leu Val Arg Asn
                405                 410                 415

Gln Asp Glu Lys Gly Gly Trp Pro Ile Met Val Thr Arg Lys Leu Gly
                420                 425                 430

Glu Gly Phe Lys Ser Leu Glu Pro Gly Trp Tyr Ser Ala Met Ala Gln
                435                 440                 445

Gly Gln Ala Ile Ser Thr Leu Val Arg Ala Tyr Leu Leu Thr Lys Asp
                450                 455                 460

Tyr Val Phe Leu Ser Ser Ala Leu Arg Ala Thr Ala Pro Tyr Lys Phe
465                 470                 475                 480

Pro Ser Glu Gln His Gly Val Lys Ala Val Phe Met Asn Lys His Asp
                485                 490                 495

Trp Tyr Glu Glu Tyr Pro Thr Thr Pro Ser Ser Phe Val Leu Asn Gly
                500                 505                 510

Phe Met Tyr Ser Leu Ile Gly Leu Tyr Asp Leu Lys Glu Thr Ala Gly
                515                 520                 525

Glu Thr Leu Gly Lys Glu Ala Arg Ser Leu Tyr Glu Arg Gly Met Glu
                530                 535                 540

Ser Leu Lys Ala Met Leu Pro Leu Tyr Asp Thr Gly Ser Gly Thr Ile
545                 550                 555                 560

Tyr Asp Leu Arg His Phe Met Leu Gly Ile Ala Pro Asn Leu Ala Arg
                565                 570                 575

Trp Asp Tyr His Thr Thr His Ile Asn Gln Leu Gln Leu Leu Ser Thr
                580                 585                 590

Ile Asp Glu Ser Pro Ile Phe Lys Glu Phe Val Lys Arg Trp Lys Ser
                595                 600                 605

Tyr Leu Lys Gly Ser Arg Ala Lys His Asn
610                 615

<210> SEQ ID NO 3
<211> LENGTH: 2239
<212> TYPE: DNA
<213> ORGANISM: Artificial sequence
<220> FEATURE:
<223> OTHER INFORMATION: Fusion protein having the sequence of the
      bovine C5-epimerase and the N-terminus of the mouse C5-epimerase

<400> SEQUENCE: 3
tggttgtcct ggaactcact ctgtagacca ggctggccat gaactcacag agatctacct    60
cctgagtgct gggattaaag gtttgtgcca ccacctccca actctaaggt gtttctttaa   120
```

-continued

```
gttaggggca tagtaaacat tgttgagata ctagaggaac actgaatgaa aatttggaca      180
tctctgcttt aggtttgtgc tgagcagttt gcctcttatc ttcacctatg ctgaaaagtt      240
tgagttcata attttgaaca tgcatatgat aaaatattct ggccgcacat tgaataaata      300
tattttaaat gaacttacct ttaaaatgtc agtaacaact ctgcatggtt ttcttcttac      360
ctccataggt atggtctgaa tatgcgttgt ttggcagctc gggtcaacta taagactttg      420
attatcatct gtgcgctatt cactttggtc acagtacttt tgtggaataa gtgttccagc      480
gacaaagcaa tccagtttcc tcggcacttg agtagtggat tcagagtgga tggattagaa      540
aaaagatcag cagcatctga agtaaccac tatgccaacc acatagccaa acagcagtca       600
gaagaggcat tcctcagga acaacagaag gcacccctg ttgttggggg cttcaatagc        660
aacgggggaa gcaaggtgtt agggctcaaa tatgaagaga ttgactgtct cataaacgat      720
gagcacacca ttaaagggag acgagagggg aatgaagttt ccttccatt cacttgggta       780 gagaaatact ttgatgttta tggaaaagtg gtccgagtat gacggctatg atcgatttga      840
attctctcat agctattcca agtctatgc acagagagcc ccttatcacc ctgatggtgt       900
gtttatgtcc tttgaaggct acaatgtgga agtccgagac agagtcaagt gcataagtgg      960
ggttgaaggt gtaccttat ctacacagtg gggacctcaa ggctatttct acccaatcca      1020
gattgcacag tatgggttaa gtcactacag caagaatcta actgaaaaac cccctcatat     1080
agaggtatat gaaacagcag aagacaggga caaaaacagc aagcccaatg actggactgt     1140
gcccaagggc tgctttatgg ctagtgtggc tgataagtca agattcacca atgttaaaca     1200
gttcattgct ccagaaacca gtgaaggtgt atccttgcaa ctggggaaca caaaagattt     1260
tattatttca tttgacctca agttcttaac aaatggaagc gtgtctgtgg ttctggagac     1320
gacagaaaag aatcagctct tcactgtaca ttatgtctca aatacccagc taattgcttt     1380
taaagaaaga gacatatact atggcatcgg gcccagaaca tcatgagca cagttacccg      1440 ggacctggtc actgacctca ggaaaggagt gggtctttcc aacacaaaag ctgtcaagcc     1500
aacaagaata atgcccaaga aggtggttag gttgattgcg aaagggaagg gcttccttga     1560
caacattacc atctctacca cagcccacat ggctgccttc ttcgctgcca gtgactggct     1620
ggtgaggaac caggatgaga aaggcggctg gccgattatg gtgacccgta agttagggga     1680
aggcttcaag tcttagagc cagggtggta ctccgccatg gcccaagggc aagccatttc      1740
tacattagtc agggcctatc tcttaacaaa agaccatata ttcctcaatt cagctttaag     1800
ggcaacagcc ccttacaagt ttctgtcaga gcagcatgga gtcaaggctg tgtttatgaa     1860
taaacatgac tggtatgaag aatatccaac tacacctagc tcttttgttt taaatggctt     1920
tatgtattct ttaattgggc tgtatgactt aaaagaaact gcagggaaa aactcgggaa      1980 agaagcgagg tccttgtatg agcgtggcat ggaatccctt aaagccatgc tccccttgta     2040
cgacactggc tcaggaacca tctatgacct ccggcacttc atgcttggca ttgccccaa      2100 cctggcccgc tgggactatc acaccaccca atcaatcaa ctgcagctgc ttagcaccat      2160
tgatgagtcc ccaatcttca aagaatttgt caagaggtgg aagagctacc ttaaaggcag     2220
ccgggcaaag cacaactag                                                  2239
```

<210> SEQ ID NO 4
<211> LENGTH: 578
<212> TYPE: PRT
<213> ORGANISM: Mus sp.

<400> SEQUENCE: 4

```
Met Arg Cys Leu Ala Ala Arg Val Asn Tyr Lys Thr Leu Ile Ile Ile
 1               5                  10                  15

Cys Ala Leu Phe Thr Leu Val Thr Val Leu Leu Ser Asp Lys Ala Ile
             20                  25                  30

Gln Phe Pro Arg His Leu Ser Ser Gly Phe Arg Val Asp Gly Leu Glu
         35                  40                  45

Lys Arg Ser Ala Ala Ser Glu Ser Asn His Tyr Ala Asn His Ile Ala
65      50                  55                  60

Lys Gln Gln Ser Glu Glu Ala Phe Pro Gln Glu Gln Lys Ala Pro
65                  70                  75                  80

Pro Val Val Gly Gly Phe Asn Ser Asn Gly Gly Ser Lys Tyr Glu Glu
                 85                  90                  95

Ile Asp Cys Leu Ile Asn Asp Glu His Thr Ile Lys Gly Arg Arg Glu
            100                 105                 110

Gly Asn Glu Val Phe Leu Pro Phe Thr Trp Val Glu Lys Tyr Phe Asp
        115                 120                 125

Val Tyr Gly Lys Val Val Gln Tyr Asp Gly Tyr Asp Arg Phe Glu Phe
130                 135                 140

Ser His Ser Tyr Ser Lys Val Tyr Ala Gln Arg Ser Pro Asp Gly Val
145                 150                 155                 160

Phe Met Ser Phe Glu Gly Tyr Asn Val Glu Val Arg Asp Arg Val Lys
                165                 170                 175

Cys Ile Ser Gly Val Glu Gly Val Pro Leu Ser Thr Gln Trp Gly Pro
            180                 185                 190

Gln Gly Tyr Phe Tyr Pro Ile Gln Ile Ala Gln Tyr Gly Leu Ser His
        195                 200                 205

Tyr Ser Lys Asn Leu Thr Glu Lys Pro Pro His Ile Glu Val Tyr Arg
210                 215                 220

Asp Arg Asn Ile Arg Pro Asn Glu Trp Thr Val Pro Lys Gly Cys Phe
225                 230                 235                 240

Met Ala Ser Val Ala Asp Lys Ser Arg Ser Thr Asn Val Lys Gln Phe
                245                 250                 255

Ile Ala Pro Glu Thr Ser Glu Gly Val Ser Leu Gln Leu Gly Asn Thr
            260                 265                 270

Lys Asp Phe Ile Ile Ser Phe Asp Asn Gly Ser Val Ser Val Val Leu
        275                 280                 285

Glu Thr Thr Glu Lys Asn Gln Leu Phe Thr Val His Tyr Val Ser Asn
290                 295                 300

Thr Gln Leu Ile Ala Phe Arg Asp Arg Asp Ile Tyr Tyr Gly Ile Gly
305                 310                 315                 320

Pro Arg Thr Ser Trp Ser Thr Val Thr Asp Leu Arg Lys Gly Val Gly
                325                 330                 335

Leu Ser Asn Thr Lys Ala Val Lys Pro Thr Lys Ile Met Pro Lys Lys
            340                 345                 350

Val Val Arg Leu Ile Ala Lys Gly Lys Gly Phe Leu Asp Asn Ile Thr
        355                 360                 365

Ile Ser Thr Thr Ala His Met Ala Ala Phe Ala Ala Ser Asp Trp
370                 375                 380

Leu Val Arg Asn Gln Asp Glu Lys Gly Ile Met Val Thr Arg Lys Leu
385                 390                 395                 400

Gly Glu Gly Phe Lys Ser Leu Glu Pro Gly Trp Tyr Ser Ala Met Ala
                405                 410                 415
```

-continued

```
Gln Gly Gln Ala Ile Ser Thr Leu Val Arg Ala Tyr Leu Leu Thr Lys
            420                 425                 430

Asp Tyr Val Phe Leu Ser Ser Ala Leu Arg Ala Thr Ala Pro Tyr Lys
            435                 440                 445

Phe Pro Ser Glu Gln His Gly Val Lys Ala Val His Asp Trp Tyr Glu
            450                 455                 460

Glu Tyr Pro Thr Thr Pro Ser Ser Phe Val Leu Asn Gly Phe Met Tyr
465                 470                 475                 480

Ser Leu Ile Gly Leu Tyr Asp Leu Lys Glu Thr Ala Gly Glu Thr Leu
            485                 490                 495

Gly Lys Glu Ala Arg Ser Leu Tyr Glu Arg Gly Met Glu Ser Leu Lys
            500                 505                 510

Ala Met Leu Pro Leu Tyr Asp Thr Gly Ser Gly Thr His Phe Met Leu
            515                 520                 525

Gly Ile Ala Pro Asn Leu Ala Arg Trp Asp Tyr His Thr Thr His Ile
            530                 535                 540

Asn Gln Leu Gln Leu Leu Ser Thr Ile Asp Glu Ser Pro Ile Phe Lys
545                 550                 555                 560

Glu Phe Val Lys Arg Trp Lys Ser Tyr Leu Lys Gly Ser Arg Ala Lys
            565                 570                 575

His Asn

<210> SEQ ID NO 5
<211> LENGTH: 434
<212> TYPE: PRT
<213> ORGANISM: Bovine lung

<400> SEQUENCE: 5

Ser His Ser Tyr Ser Lys Val Tyr Ala Gln Arg Ala Pro Asp Gly Val
1               5                   10                  15

Phe Met Ser Phe Glu Gly Tyr Asn Val Glu Val Arg Asp Arg Val Lys
            20                  25                  30

Cys Ile Ser Gly Val Glu Gly Val Pro Leu Ser Thr Gln Trp Gly Pro
            35                  40                  45

Gln Gly Tyr Phe Tyr Pro Ile Gln Ile Ala Gln Tyr Gly Leu Ser His
            50                  55                  60

Tyr Ser Lys Asn Leu Thr Glu Lys Pro Pro His Ile Glu Val Tyr Arg
65                  70                  75                  80

Asp Lys Asn Ser Lys Pro Asn Asp Trp Thr Val Pro Lys Gly Cys Phe
            85                  90                  95

Met Ala Ser Val Ala Asp Lys Ser Arg Phe Thr Asn Val Lys Gln Phe
            100                 105                 110

Ile Ala Pro Glu Thr Ser Glu Gly Val Ser Leu Gln Leu Gly Asn Thr
            115                 120                 125

Lys Asp Phe Ile Ile Ser Phe Asp Asn Gly Ser Val Ser Val Val Leu
            130                 135                 140

Glu Thr Thr Glu Lys Asn Gln Leu Phe Thr Val His Tyr Val Ser Asn
145                 150                 155                 160

Thr Gln Leu Ile Ala Phe Lys Glu Arg Asp Ile Tyr Tyr Gly Ile Gly
            165                 170                 175

Pro Arg Thr Ser Trp Ser Thr Val Thr Asp Leu Arg Lys Gly Val Gly
            180                 185                 190

Leu Ser Asn Thr Lys Ala Val Lys Pro Thr Arg Ile Met Pro Lys Lys
            195                 200                 205
```

-continued

```
Val Val Arg Leu Ile Ala Lys Gly Lys Gly Phe Leu Asp Asn Ile Thr
    210                 215                 220
Ile Ser Thr Thr Ala His Met Ala Ala Phe Phe Ala Ala Ser Asp Trp
225                 230                 235                 240
Leu Val Arg Asn Gln Asp Glu Lys Gly Ile Met Val Thr Arg Lys Leu
                245                 250                 255
Gly Glu Gly Phe Lys Ser Leu Glu Pro Gly Trp Tyr Ser Ala Met Ala
            260                 265                 270
Gln Gly Gln Ala Ile Ser Thr Leu Val Arg Ala Tyr Leu Leu Thr Lys
        275                 280                 285
Asp His Ile Phe Leu Asn Ser Ala Leu Arg Ala Thr Ala Pro Tyr Lys
    290                 295                 300
Phe Leu Ser Glu Gln His Gly Val Lys Ala Val His Asp Trp Tyr Glu
305                 310                 315                 320
Glu Tyr Pro Thr Thr Pro Ser Ser Phe Val Leu Asn Gly Phe Met Tyr
                325                 330                 335
Ser Leu Ile Gly Leu Tyr Asp Leu Lys Glu Thr Ala Gly Glu Lys Leu
            340                 345                 350
Gly Lys Glu Ala Arg Ser Leu Tyr Glu Arg Gly Met Glu Ser Leu Lys
        355                 360                 365
Ala Met Leu Pro Leu Tyr Asp Thr Gly Ser Gly Thr His Phe Met Leu
    370                 375                 380
Gly Ile Ala Pro Asn Leu Ala Arg Trp Asp Tyr His Thr Thr His Ile
385                 390                 395                 400
Asn Gln Leu Gln Leu Leu Ser Thr Ile Asp Glu Ser Pro Ile Phe Lys
                405                 410                 415
Glu Phe Val Lys Arg Trp Lys Ser Tyr Leu Lys Gly Ser Arg Ala Lys
            420                 425                 430
His Asn
```

<210> SEQ ID NO 6
<211> LENGTH: 569
<212> TYPE: PRT
<213> ORGANISM: Homo sapiens

<400> SEQUENCE: 6

```
Asn Tyr Lys Thr Leu Ile Ile Cys Ala Leu Phe Thr Leu Val Thr
1               5                   10                  15
Val Leu Leu Ser Asp Lys Ala Ile Gln Phe Pro Arg Arg Ser Ser Ser
                20                  25                  30
Gly Phe Arg Val Asp Gly Phe Glu Lys Arg Ala Ala Ala Ser Glu Ser
            35                  40                  45
Asn Asn Tyr Met Asn His Val Ala Lys Gln Gln Ser Glu Glu Ala Phe
        50                  55                  60
Pro Gln Glu Gln Gln Lys Ala Pro Pro Val Val Gly Gly Phe Asn Ser
65                  70                  75                  80
Asn Val Gly Ser Lys Tyr Glu Glu Ile Asp Cys Leu Ile Asn Asp Glu
                85                  90                  95
His Thr Ile Lys Gly Arg Arg Glu Gly Asn Glu Val Phe Leu Pro Phe
            100                 105                 110
Thr Trp Val Glu Lys Tyr Phe Asp Val Tyr Gly Lys Val Val Gln Tyr
        115                 120                 125
Asp Gly Tyr Asp Arg Phe Glu Phe Ser His Ser Tyr Ser Lys Val Tyr
    130                 135                 140
```

-continued

```
Ala Gln Arg Ala Pro Asp Gly Val Phe Met Ser Phe Glu Gly Tyr Asn
145                 150                 155                 160

Val Glu Val Arg Asp Arg Val Lys Cys Ile Ser Gly Val Glu Gly Val
                165                 170                 175

Pro Leu Ser Thr Gln Trp Gly Pro Gln Gly Tyr Phe Tyr Pro Ile Gln
            180                 185                 190

Ile Ala Gln Tyr Gly Leu Ser His Tyr Ser Lys Asn Leu Thr Glu Lys
        195                 200                 205

Pro Pro His Ile Glu Val Tyr Arg Asp Lys Asn Lys Pro Asn Asp Trp
    210                 215                 220

Thr Val Pro Lys Gly Cys Phe Met Ala Asn Val Ala Asp Lys Ser Arg
225                 230                 235                 240

Phe Thr Asn Val Lys Gln Phe Ile Ala Pro Glu Thr Ser Glu Gly Val
                245                 250                 255

Ser Leu Gln Leu Gly Asn Thr Lys Asp Phe Ile Ile Ser Phe Asp Asn
            260                 265                 270

Gly Ser Val Ser Val Val Leu Glu Thr Thr Glu Lys Asn Gln Leu Phe
        275                 280                 285

Thr Ile His Tyr Val Ser Asn Ala Gln Leu Ile Ala Phe Lys Glu Arg
    290                 295                 300

Asp Ile Tyr Tyr Gly Ile Gly Pro Arg Thr Ser Trp Ser Thr Val Thr
305                 310                 315                 320

Asp Leu Arg Lys Gly Val Gly Leu Ser Asn Thr Lys Ala Val Lys Pro
                325                 330                 335

Thr Lys Ile Met Pro Lys Lys Val Val Arg Leu Ile Ala Lys Gly Lys
            340                 345                 350

Gly Phe Leu Asp Asn Ile Thr Ile Ser Thr Thr Ala His Met Ala Ala
        355                 360                 365

Phe Phe Ala Ala Ser Asp Trp Leu Val Arg Asn Gln Asp Glu Lys Gly
    370                 375                 380

Ile Met Val Thr Arg Lys Leu Gly Glu Gly Phe Lys Ser Leu Glu Pro
385                 390                 395                 400

Gly Trp Tyr Ser Ala Met Ala Gln Gly Gln Ala Ile Ser Thr Leu Val
                405                 410                 415

Arg Ala Tyr Leu Leu Thr Lys Asp His Ile Phe Leu Asn Ser Ala Leu
            420                 425                 430

Arg Ala Thr Ala Pro Tyr Lys Phe Leu Ser Glu Gln His Gly Val Lys
        435                 440                 445

Ala Val His Asp Trp Tyr Glu Glu Tyr Pro Thr Thr Pro Ser Ser Phe
    450                 455                 460

Val Leu Asn Gly Phe Met Tyr Ser Leu Ile Gly Leu Tyr Asp Leu Lys
465                 470                 475                 480

Glu Thr Ala Gly Glu Lys Leu Gly Lys Glu Ala Arg Ser Leu Tyr Glu
                485                 490                 495

Arg Gly Met Glu Ser Leu Lys Ala Met Leu Pro Leu Tyr Asp Thr Gly
            500                 505                 510

Ser Gly Thr His Phe Met Leu Gly Ile Ala Pro Asn Leu Ala Arg Trp
        515                 520                 525

Asp Tyr His Thr His Ile Asn Gln Leu Gln Leu Ser Thr Ile
    530                 535                 540

Asp Glu Ser Pro Ile Phe Lys Glu Phe Val Lys Arg Trp Lys Ser Tyr
545                 550                 555                 560
```

-continued

```
Leu Lys Gly Ser Arg Ala Lys His Asn
            565

<210> SEQ ID NO 7
<211> LENGTH: 576
<212> TYPE: PRT
<213> ORGANISM: Drosophila sp.

<400> SEQUENCE: 7

Met Ser Lys Tyr Leu Ser Ser Gln Arg Asp Ala Leu Ser Ala Pro Ala
1               5                   10                  15

Leu Pro Val Ser Arg Glu Asn Arg Glu Pro Pro Lys Phe Gln Gly Val
            20                  25                  30

Lys Gln Arg Glu Pro Leu Val Phe Phe Ile Met Arg Leu Asn Leu Lys
        35                  40                  45

Ala Val Leu Leu Val Leu Thr Val Ala Val Val Ile Thr Leu Gly
    50                  55                  60

Val Ala Phe Ser Phe Ser Pro Asp Phe Val Pro Leu Asp Arg Ser
65                  70                  75                  80

Ala Arg Gln Ser Ser Ser Gly Gly Glu His Asp Ile Glu Cys Ser Ile
                85                  90                  95

Asn Gln Glu Tyr Thr Val His Cys Lys Arg Asp Glu Asn Ala Asn Glu
            100                 105                 110

Val Tyr Val Pro Phe Ser Phe Leu Arg Asn Tyr Phe Asp Val Ser Gly
        115                 120                 125

Ala Val Ser Thr Asn Ser Asn Glu Val Ala Lys Phe Asn Trp Val His
    130                 135                 140

Ser Thr Ala Lys Val Asn Leu Pro Arg Gly Lys Arg Gly Val Tyr Met
145                 150                 155                 160

Tyr Phe Glu Asn Tyr Asn Val Glu Val Arg Asp Arg Val Lys Cys Ile
                165                 170                 175

Ser Ala Ala Glu Gly Val Pro Val Ser Thr Gln Trp Glu Lys Arg Gly
            180                 185                 190

Tyr Phe Tyr Pro Thr Gln Ile Ala Gln Phe Ala Leu Ser His Tyr Ser
        195                 200                 205

Lys Asn Leu Thr Glu Pro Ala Pro Arg Val Arg Val Leu Gly Asp Gly
    210                 215                 220

Asn Gln Met Glu Trp Ser Thr Pro Lys Thr Ser Asn Met Thr Arg Ile
225                 230                 235                 240

Trp His His Lys Phe Asn Thr Ser Val Val Gln Phe Glu Thr Ala Pro
                245                 250                 255

Gly Tyr Glu Gly Val Ile Ser Ile Ala Leu Asn Gln Thr Leu Asp Leu
            260                 265                 270

Leu Leu Ser Val Asp Asn Ser Ser Leu Met Ile Thr Val Gln Asn
        275                 280                 285

Arg Asp Thr Arg His Asn Tyr Ser Leu His Tyr Ile Pro Ala Asp Leu
    290                 295                 300

Leu Leu Ser Val Gln Asp Thr Asn Ile Tyr Tyr Gly Leu Gly Gly Ser
305                 310                 315                 320

Ala Leu Asn Lys Trp Arg His Ile Thr Asp Leu Gln Lys Gly Ile Met
                325                 330                 335

Gly Asp Lys Arg Ser Pro Leu Lys Ile Arg Arg Ser Asp Leu Glu Val
            340                 345                 350

Ile Ser Ile Gly Phe Leu Gly Leu Gly Phe Phe Asp Asn Ile Thr Leu
        355                 360                 365
```

```
Ser Thr Ser Asp His Leu Ala His Phe Tyr Asp Ala Ala Glu Trp Phe
        370                 375                 380

Val His Asn Gln Asp Pro Lys Thr Gly Val Arg Arg Ser Leu Asn Gly
385                 390                 395                 400

Phe Ala Glu Leu Arg Pro Gly Trp Ile Ser Ala Met Gly Gln Gly His
                405                 410                 415

Ala Ile Ser Val Leu Ala Arg Ala Tyr Trp His Ser Gly Gly Asp Glu
            420                 425                 430

Arg Tyr Leu Arg Ala Ala Ala Gly Leu Gln Pro Tyr Arg Val Tyr
        435                 440                 445

Ser Arg Asp Gly Gly Val Leu Ala Gln Phe Tyr Trp Tyr Glu Glu Tyr
450                 455                 460

Pro Thr Thr Pro Pro Ser Tyr Val Leu Asn Gly Phe Ile Tyr Ser Leu
465                 470                 475                 480

Leu Gly Leu Tyr Asp Leu Asn Ser Thr Ala Pro Gly Lys Ile Ala Arg
                485                 490                 495

Glu Ala Gly Lys Leu Phe Ala Gln Gly Met His Ser Leu Lys Lys Met
            500                 505                 510

Leu Leu Leu Phe Asp Thr Gly Ser Gly Thr His Leu Ser Leu Gly Val
        515                 520                 525

Ala Pro Asn Leu Ala Arg Trp Asp Tyr His Ala Thr His Val Asn Gln
530                 535                 540

Leu Leu Leu Leu Ala Thr Ile Asp Ser Asp Pro Leu Ile Ala Gln Thr
545                 550                 555                 560

Ala Glu Arg Trp Lys Gly Tyr Met Phe Gly Arg Arg Ala Lys His Asn
                565                 570                 575

<210> SEQ ID NO 8
<211> LENGTH: 599
<212> TYPE: PRT
<213> ORGANISM: C. elegans

<400> SEQUENCE: 8

Met Val Leu Val Ser Leu Lys Pro Phe Asn Ile Phe Ser Leu Lys Pro
1               5                   10                  15

Met Lys Cys Leu Arg Trp Arg Ser Asn Arg His Arg Ile Tyr Leu Leu
            20                  25                  30

Val Ala Cys Gly Ala Leu Phe Leu Arg His Leu Thr Gln Glu Glu
        35                  40                  45

Ser Arg Ile Asp Glu Glu Asp Glu Glu Leu Thr Gln Val Asp Val Asn
50                  55                  60

Glu Asp Asp Lys Lys Ile Glu Cys Glu Pro Pro Gly Ser Ile Glu Ser
65                  70                  75                  80

Lys Cys Ile Ala Asp Asn Gly Lys Ser Met Lys Cys Trp Lys Asp Glu
                85                  90                  95

Glu Asp Val Tyr Phe Pro Val Ser Tyr Leu Lys Arg Phe Asp Met
            100                 105                 110

Thr Gly Lys Leu Gly Lys Asp Gly Ser Thr Phe Glu Leu Tyr Thr Ser
        115                 120                 125

Tyr Ala Lys Met Arg Ser Pro Asp Leu Gly Pro Phe Gly His Phe Ser
130                 135                 140

Thr Tyr Ser Val Glu Thr Arg Asp Arg Val Arg Cys Val Ser Ala Lys
145                 150                 155                 160

Thr Asp Val Pro Met Ser Thr Gln Trp Asp Pro Ile Pro Tyr Tyr Tyr
```

-continued

```
                165                 170                 175
Pro Ile Gln Ile Ser Gln Tyr Gly Leu Gln His Tyr Ser Arg Met Lys
            180                 185                 190
Leu Asp Ser Ile Ser Asn Lys Ser Glu Ala Ser Pro Lys Asp Asp Val
            195                 200                 205
Ile Asn Ser Lys Glu Trp Lys Gly Ala Ala Gly Met His Glu Thr Thr
            210                 215                 220
Glu Arg Leu Phe Phe Asn Asp Glu Gln Met Gly Lys Val Val Asn Ile
225                 230                 235                 240
Ser Ala Gly Ala Ala Leu Ala Asn Ala Gly Ala Tyr Val Tyr Leu Asp
            245                 250                 255
Lys Ser Pro Asp Leu His Val Ile Ser Phe Asp Ala Asn Ser Ser Phe
            260                 265                 270
Thr Val Leu Ala Lys Met Lys Gln Asp Asp Leu Leu Val Leu Ile Asn
            275                 280                 285
Tyr Val Tyr Ser Glu Gly Asn Gly Lys Cys Val Trp Gln Glu Glu Glu
            290                 295                 300
Arg Ile Ser Asp Asp Tyr Ile Val Gln Lys Pro Lys Lys Asp Gly Gln
305                 310                 315                 320
Val Ser Tyr Ser Tyr Ser Tyr Ile Gly Asn Ser Pro Ile Gly Glu Trp
            325                 330                 335
Ser Thr Val Thr Asp Val Ala Arg Ala Leu Ser Ser Gly Asp Asn Arg
            340                 345                 350
Lys Lys Asp Asp Asn Val Val Leu His Ala Gly Asp Leu Arg Leu Val
            355                 360                 365
Ser Leu Gly Phe Arg Gly Glu Leu Thr Val Lys Gln Lys Ile Thr Gln
            370                 375                 380
Arg Arg Glu Gln His Ser His Ala Phe Tyr Ala Ala Asp Trp Leu
385                 390                 395                 400
Val Lys Asn Gln Asn Asp Arg Gly Val Glu Arg Ser Ile Ala Glu Arg
            405                 410                 415
Lys Leu Val Leu Pro Pro Gly Trp His Ser Ala Met Ala Gln Gly His
            420                 425                 430
Gly Ile Ser Val Leu Thr Arg Ala Phe Lys His Phe Asn Asp Glu Lys
            435                 440                 445
Tyr Leu Lys Ser Ala Ala Lys Ala Leu Lys Leu Phe Lys Ile Asn Ser
            450                 455                 460
Ser Asp Gly Gly Val Arg Gly Glu Ile Trp Tyr Glu Glu Tyr Pro Thr
465                 470                 475                 480
Thr Pro Gly Ser Phe Val Leu Asn Gly Phe Leu Tyr Ser Leu Ile Gly
            485                 490                 495
Leu Tyr Asp Leu Ser Gln Leu Glu Leu Met Ile Asp Glu Asn Asp Glu
            500                 505                 510
Thr Met Arg Ala Lys Ile Gln Glu Ala Gln Glu Leu Tyr Ser Ala Gly
            515                 520                 525
Val Arg Ser Leu Lys Gln Leu Leu Pro Leu Tyr Asp Thr Gly Ser Gly
            530                 535                 540
Thr His Val Ala Leu Gly Thr Ala Pro Asn Leu Ala Arg Trp Asp Tyr
545                 550                 555                 560
His Ala Val His Val Tyr Leu Leu Lys Trp Ile Ala Gly Ile Glu Lys
            565                 570                 575
Asp Glu Val Leu Ser Lys Thr Ala Asp Arg Trp Ile Gly Tyr Ala Tyr
            580                 585                 590
```

Gly Lys Arg Ala Lys His Asn
        595

<210> SEQ ID NO 9
<211> LENGTH: 216
<212> TYPE: PRT
<213> ORGANISM: Methanococcus sp.

<400> SEQUENCE: 9

Met Ile Leu Met Lys Lys Phe Glu Ile Ile Leu Phe Leu Phe Ile Ala
1               5                   10                  15

Val Leu Ile Phe Val Phe Gly Phe Val Gly Ala Ser Gln Pro Leu Tyr
            20                  25                  30

Ser Glu Asn Pro Val Ile Gln Tyr Phe Lys Asn Pro Lys Pro Phe Thr
        35                  40                  45

Val Glu Asn Val Asn Met Pro Val Thr Tyr Tyr Gly Thr Ile Cys Gly
    50                  55                  60

Lys Tyr Ile Gly Tyr Gln Ile Thr Pro His Asn Val Asn Glu Glu Ala
65                  70                  75                  80

Arg Lys Cys Phe Tyr Lys Tyr Phe Lys Leu Lys Asp Lys Asn Pro Lys
                85                  90                  95

Glu Ala Glu Arg Tyr Leu Lys Arg Gly Leu Phe Leu Thr Glu Tyr Leu
            100                 105                 110

Ile Ser Gln Ala Asp Lys Glu Thr Ala Glu Val Asp Glu Lys Asn Ile
        115                 120                 125

Thr Phe Ile Val Trp Arg Tyr Asn Phe Glu Phe Pro Asn Leu Ser Lys
    130                 135                 140

Gly Trp Arg Gly Ala Leu Cys Gln Ala Gly Cys Leu Lys Thr Leu Tyr
145                 150                 155                 160

Leu Ala Tyr Glu Ala Thr Gly Asp Glu Arg Tyr Leu Asn Tyr Ala Asn
                165                 170                 175

Leu Ala Ile Asn Ala Phe Lys Val Pro Val Glu Lys Gly Gly Leu Leu
            180                 185                 190

Lys Ile Arg Ile Tyr Tyr Trp Phe Pro Glu Tyr Ala Ser Glu Asn Pro
        195                 200                 205

Pro Tyr Val Leu Asn Gly Phe Ile
    210                 215

<210> SEQ ID NO 10
<211> LENGTH: 174
<212> TYPE: DNA
<213> ORGANISM: Artificial sequence
<220> FEATURE:
<223> OTHER INFORMATION: Tag that preceded each recombinant construct
<220> FEATURE:
<221> NAME/KEY: CDS
<222> LOCATION: (1)..(174)

<400> SEQUENCE: 10 atg act att ctc tgc tgg ctt gcg ctg ttg tca aca ctt acc gcc gtg      48
Met Thr Ile Leu Cys Trp Leu Ala Leu Leu Ser Thr Leu Thr Ala Val
1               5                   10                  15 aac gca gac tac aag gac gac gat gac aag cgg ccg cat gcg gaa ttc      96
Asn Ala Asp Tyr Lys Asp Asp Asp Asp Lys Arg Pro His Ala Glu Phe
            20                  25                  30 atg cgg ggt tct cat cac cat cac cat cac gat tac gat atc cca acg     144
Met Arg Gly Ser His His His His His His Asp Tyr Asp Ile Pro Thr
        35                  40                  45

-continued

```
acc gaa aac ctg tat ttt cag ggc gcc atg                                    174
Thr Glu Asn Leu Tyr Phe Gln Gly Ala Met
    50                  55

<210> SEQ ID NO 11
<211> LENGTH: 58
<212> TYPE: PRT
<213> ORGANISM: Artificial sequence
<220> FEATURE:
<223> OTHER INFORMATION: Tag that preceded each recombinant construct

<400> SEQUENCE: 11

Met Thr Ile Leu Cys Trp Leu Ala Leu Leu Ser Thr Leu Thr Ala Val
1               5                   10                  15

Asn Ala Asp Tyr Lys Asp Asp Asp Lys Arg Pro His Ala Glu Phe
            20                  25                  30

Met Arg Gly Ser His His His His His His Asp Tyr Asp Ile Pro Thr
        35                  40                  45

Thr Glu Asn Leu Tyr Phe Gln Gly Ala Met
    50                  55
```